United States Patent
Yoshioka

(10) Patent No.: US 11,186,618 B2
(45) Date of Patent: Nov. 30, 2021

(54) DENDRITIC-CELL-TARGETED PEPTIDE, FUSION PEPTIDE UTILIZING SAID PEPTIDE, AND VACCINE UTILIZING SAID FUSION PEPTIDE

(71) Applicant: The Research Foundation for Microbial Diseases of Osaka University, Suita (JP)

(72) Inventor: Yasuo Yoshioka, Suita (JP)

(73) Assignee: THE RESEARCH FOUNDATION FOR MICROBIAL DISEASES OF OSAKA UNIVERSITY, Suita (JP)

( * ) Notice: Subject to any disclaimer, the term of this patent is extended or adjusted under 35 U.S.C. 154(b) by 24 days.

(21) Appl. No.: 16/335,625

(22) PCT Filed: Sep. 21, 2017

(86) PCT No.: PCT/JP2017/034069
§ 371 (c)(1),
(2) Date: Mar. 21, 2019

(87) PCT Pub. No.: WO2018/056351
PCT Pub. Date: Mar. 29, 2018

(65) Prior Publication Data
US 2019/0300585 A1 Oct. 3, 2019

(30) Foreign Application Priority Data

Sep. 21, 2016 (JP) .............................. JP2016-183942
Jun. 30, 2017 (JP) .............................. JP2017-129202

(51) Int. Cl.
| C07K 14/415 | (2006.01) |
| A61K 9/00 | (2006.01) |
| C07K 14/36 | (2006.01) |
| C07K 14/315 | (2006.01) |
| C07K 19/00 | (2006.01) |
| A61P 37/04 | (2006.01) |
| C07K 7/06 | (2006.01) |
| A61K 47/50 | (2017.01) |
| A61K 39/00 | (2006.01) |
| C12P 21/02 | (2006.01) |
| C12N 15/09 | (2006.01) |

(52) U.S. Cl.
CPC ............ *C07K 14/415* (2013.01); *A61K 9/007* (2013.01); *A61K 39/00* (2013.01); *A61K 47/50* (2017.08); *A61P 37/04* (2018.01); *C07K 7/06* (2013.01); *C07K 14/315* (2013.01); *C07K 14/36* (2013.01); *C07K 19/00* (2013.01); *C12N 15/09* (2013.01); *C12P 21/02* (2013.01)

(58) Field of Classification Search
None
See application file for complete search history.

(56) References Cited

FOREIGN PATENT DOCUMENTS

WO WO 2012/068236 A2 5/2012

OTHER PUBLICATIONS

Database Uniprot, Accession No. A0A093VPE1, dated Nov. 26, 2014.
Database Uniprot, Accession No. A0A177D8A2, dated Sep. 7, 2016.
Database Uniprot, Accession No. B2WHB2, dated Jul. 1, 2008.
Database Uniprot, Accession No. B6JWN8, dated Dec. 16, 2008.
Database Uniprot, Accession No. B8MCA2, dated Mar. 3, 2009.
International Search Report in PCT/JP2017/034069, dated Dec. 19, 2017.
Misato, K. et al. 2016 "Vaccine adjuvant effects of dendritic cell-targeting peptides identified by means of phage display" p. 44, Abstract No. 1-B-W3-25-P, Proceedings of Academic Meeting of the Japanese Society for Immunology.
Misato, K. et al., 2016 "Development of novel peptide-based adjuvants utilizing phage surface display method" Abstracts of the Annual Meeting of the Japanese Society for Vaccinology.
Sioud, M. et al. 2013 "A novel peptide carrier for efficient targeting of antigens and nucleic acids to dendritic cells" FASEB J., vol. 27, pp. 3272-3283.
Sugahara, K.N. et al., 2009 "Tissue-penetrating delivery of compounds and nanoparticles into tumors" Cancer cell, vol. 16, No. 5, 510-520.
Yan, Z. et al., 2016 "A novel peptide targeting Clec9a on dendritic cell for cancer immunotherapy", Oncotarget, 2016, vol. 7, No. 26, pp. 40437-40450.
Search Report issued for counterpart European Patent Application No. 17853120.8 (dated Apr. 15, 2020).
Brooks, N A, et al., 2010 "Cell-Penetrating peptides: Application in vaccine delivery," Biochimica et Biophysica Acta vol. 1805: 25-34.
Kartik Sehgal, et al., "Targeting human dendritic cells in situ to improve vaccines," Immunology Letters, vol. 162, No. 1, Nov. 1, 2014, pp. 59-67.
Sangho Lim, et al., "Use of Cell-Penetrating Peptides in Dendritic Cell-Based Vaccination", Immune Network, vol. 16, No. 1, Feb. 2016, pp. 33-43.

*Primary Examiner* — Robert A Zeman
(74) *Attorney, Agent, or Firm* — Knobbe, Martens, Olson & Bear, LLP

(57) ABSTRACT

The purpose of the present invention is to provide a peptide that is capable of efficiently delivering an antigen to dendritic cells and improving the vaccine effects of the antigen. A peptide that has at least one motif sequence comprising the amino acid sequence of sequence listing 1, or an amino acid sequence comprising the aforementioned amino acid sequence, but in which a mutation has been induced in the amino acid residue at the first and/or second position of the amino acid sequence, is bound to an antigen protein or an antigen peptide to efficiently deliver the antigen protein or antigen peptide to dendritic cells, allowing for significantly superior vaccine effects to be exhibited.

10 Claims, 10 Drawing Sheets

Specification includes a Sequence Listing.

| FL4 | VSYKAIR |
| Mut 1 | ASYKAIR |
| Mut 2 | VAYKAIR |
| Mut 3 | VSAKAIR |
| Mut 4 | VSYKAAR |

DENDRITIC-CELL-TARGETED PEPTIDE, FUSION PEPTIDE UTILIZING SAID PEPTIDE, AND VACCINE UTILIZING SAID FUSION PEPTIDE

TECHNICAL FIELD

The present invention relates to a peptide that is capable of delivering an antigen to dendritic cells efficiently and improving vaccine effects of the antigen. The present invention also relates to a fusion peptide in which the peptide is bound to an antigenic protein or an antigenic peptide, and a vaccine using the fusion peptide.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 30173900_1.TXT, the date of creation of the ASCII text file is Mar. 21, 2019, and the size of the ASCII text file is 9.94 KB.

BACKGROUND ART

The fundamental principle of prevention of infectious diseases and cancer by vaccines is to induce adaptive immunity by artificial mock infection and to induce antibody production and cellular immunity against specific pathogens. In recent years, with regard to prevention of infectious diseases by vaccines, expectations are being made for vaccine development that uses pathogen-derived proteins or peptides as antigens instead of pathogens themselves, without using live vaccines such as those using attenuated strains and the like, because of the emphasis on safety.

However, even when a protein or a peptide that serves as an antigen is administered alone, it is hardly transferred to lymph nodes where immunity is induced. Accordingly, it is not taken into dendritic cells which are immunocompetent cells, and therefore, it is difficult to induce an immune response. Accordingly, in developing a vaccine, it is essential to control biokinetics of the antigen. Further, in order to induce protective immunity against a pathogen sufficiently, it is important to use an immunostimulant (adjuvant) in combination. However, lack of adjuvants that can induce sufficient immune responses has become one of the major barriers in vaccine development.

Conventionally, attempts have been made to utilize a peptide as a carrier for delivering an antigen to dendritic cells efficiently. For example, Non-Patent Document 1 discloses that the peptide WH (amino acid sequence: WPRFHSSVFHTH; SEQ ID NO: 7) can selectively bind to Clec9a expressed on dendritic cells, so that the peptide can be used as a carrier peptide to dendritic cells. In addition, Non-Patent Document 2 discloses that the NW peptide (amino acid sequence: NWYLPWLGTNDW; SEQ ID NO: 8) has a high binding ability to dendritic cells and can be used for delivery of an antigen to dendritic cells. However, the carrier peptides disclosed in Non-Patent Documents 1 and 2 have a disadvantage that vaccine effects cannot be sufficiently exhibited unless each of the peptides is used in combination with an adjuvant.

On the other hand, Non-Patent Document 3 reports that Neuropilin-1 is expressed on cancer cells, and a peptide having a motif sequence consisting of R/K-X-X-R/K (SEQ ID NO: 9, X is an arbitrary amino acid) binds to Neuropilin-1 on the cancer cell surface, and therefore, the peptide is incorporated into cancer cells. Accordingly, drug delivery to cancer tissues by using the peptide having the motif sequence has been attempted.

It is also known that Neuropilin-1 is also expressed on some immune cells (dendritic cells, and regulatory T cells). However, there has been no research so far applied to immune regulation with regard to a peptide having a motif sequence consisting of R/K-X-X-R/K (SEQ ID NO: 9).

PRIOR ART DOCUMENTS

Non-Patent Documents

Non-Patent Document 1: Zhongyi et al., A novel peptide targeting Clec9a on dendritic cell for cancer immunotherapy. Oncotarget, Vol. 7, No. 26, 40437-40450

Non-Patent Document 2: Sioud et al., A novel peptide carrier for efficient targeting of antigens and nucleic acids to dendritic cells. FASEB J., Vol. 27, 3272-3283

Non-Patent Document 3: Sugahara et al., Tissue-penetrating delivery of compounds and nanoparticles into tumors. Cancer cell, Vol. 16, No. 5, 510-520

SUMMARY OF THE INVENTION

Problems to be Solved by the Invention

An object of the present invention is to provide a peptide (carrier peptide) that is capable of delivering an antigen to dendritic cells efficiently and improving vaccine effects of an antigenic protein or an antigenic peptide. Further, an object of the present invention is to provide a fusion peptide in which the peptide is bound to an antigenic protein or an antigenic peptide, and a vaccine preparation using the fusion peptide.

Means for Solving the Problem

The present inventor has conducted intensive studies to solve the above problems. Specifically, the present inventor has identified about 30 kinds of peptides as possible peptides which are capable of binding to dendritic cells selectively, by firstly conducting a comprehensive screening method that uses a phage library on the surface of which about 1 billion kinds of random peptides consisting of random 7 or less amino acids are displayed. Many of the identified peptides had a motif sequence consisting of R/K-X-X-R/K (SEQ ID NO: 9, X is an arbitrary amino acid). Subsequently, each of the identified peptides was bound to an antigenic protein or an antigenic peptide and the mouse was immunized by using the same. As a result, only when a peptide having an amino acid sequence consisting of SEQ ID NO: 1 was used, a remarkably excellent immune response was induced. This peptide had different effects from other peptides having the motif sequence consisting of R/K-X-X-R/K (SEQ ID NO: 9). Further, it was confirmed that a fusion peptide in which a peptide having an amino acid sequence consisting of SEQ ID NO: 1 was bound to an antigenic protein or an antigenic peptide was capable of exhibiting excellent vaccine effects even though no adjuvant was used in some cases. The present invention has been completed by further investigation based on these findings.

Namely, the present invention provides the following embodiments of the invention.

Item 1. A peptide including at least one motif sequence selected from amino acid sequences shown in the following (i) and (ii):

(i) an amino acid sequence shown in SEQ ID NO: 1; and
(ii) an amino acid sequence that is derived from an amino acid sequence shown in SEQ ID NO: 1 of which at least one amino acid residue at positions 1 and 2 is substituted by an alanine residue.

Item 2. The peptide according to item 1, which has 1 to 5 motif sequences consisting of the amino acid sequence shown in (i).

Item 3. A DNA molecule encoding the peptide according to item 1 or 2.

Item 4. A fusion peptide in which the peptide according to item 1 or 2 is bound to an antigenic protein or an antigenic peptide.

Item 5. The fusion peptide according to item 4, in which the N-terminus of the peptide according to item 1 or 2 is bound to the C-terminal side of the antigenic protein or the antigenic peptide.

Item 6. The fusion peptide according to item 4 or 5, wherein the antigenic protein or the antigenic peptide is a cancer antigenic protein or a cancer antigenic peptide.

Item 7. The fusion peptide according to item 4 or 5, wherein the antigenic protein or the antigenic peptide is an antigenic protein or an antigenic peptide of a pathogenic virus.

Item 8. The fusion peptide according to item 4 or 5, wherein the antigenic protein or the antigenic peptide is an antigenic protein or an antigenic peptide of a pathogenic bacterium.

Item 9. A vaccine preparation including the fusion peptide according to any one of items 4 to 8.

Item 10. The vaccine preparation according to item 9, which is for pulmonary administration.

Advantages of the Invention

Since the peptide of the present invention can selectively bind to dendritic cells, an antigenic protein or an antigenic peptide can be efficiently delivered to dendritic cells by being fused with the peptide of the present invention. In addition, the peptide of the present invention has a remarkably high effect of inducing an immune response by the bound antigenic protein or antigenic peptide, and it is recognized that excellent vaccine effects are exhibited without using an adjuvant in some cases. As described above, since the peptide of the present invention is capable of delivering an antigenic protein or an antigenic peptide to dendritic cells efficiently, and exhibiting excellent vaccine effects, the dose of the antigenic protein or the antigenic peptide can be reduced. Such effects are not recognized when other peptides having a motif sequence consisting of R/K-X-X-R/K (SEQ ID NO: 9) are used, and are unique to the peptide of the invention of the present application.

EMBODIMENTS OF THE INVENTION

Figure 1:
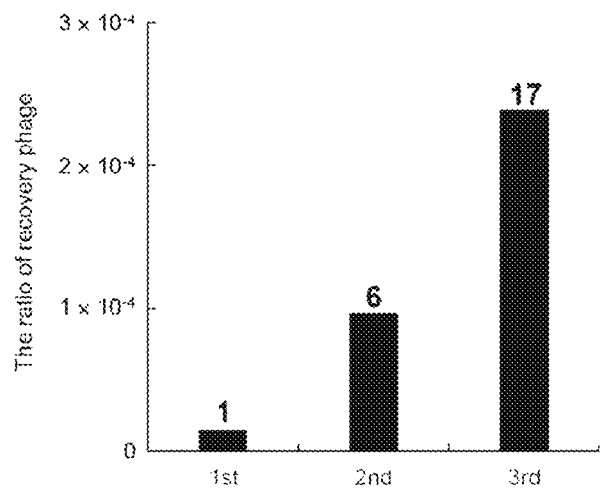
FIG. 1 shows a diagram showing results of performing a panning operation three times to obtain phages to which dendritic cells are bound and determining the number of phages recovered in each operation number in Test Example 1.

Hereinafter, the present invention is described in detail. Meanwhile, in the specification other than the sequence listing, 20 kinds of amino acid residues in the amino acid sequence may be sometimes represented by one letter abbreviation.

Namely, glycine (Gly) is G, alanine (Ala) is A, valine (Val) is V, leucine (Leu) is L, isoleucine (Ile) is I, phenylalanine (Phe) is F, tyrosine (Tyr) is Y, tryptophan (Trp) is W, serine (Ser) is S, threonine (Thr) is T, cysteine (Cys) is C, methionine (Met) is M, aspartic acid (Asp) is D, glutamic acid (Glu) is E, asparagine (Asn) is N, glutamine (Gln) is Q, lysine (Lys) is K, arginine (Arg) is R, histidine (His) is H, and proline (Pro) is P.

In addition, in the present specification, in the amino acid sequence to be displayed, the N-terminus is the left end and the C-terminus is the right end.

1. Peptide (Carrier Peptide)

[Amino Acid Sequence]

The peptide of the present invention is a peptide including at least one motif sequence selected from amino acid sequences shown in the following (i) and (ii):

(i) an amino acid sequence shown in SEQ ID NO: 1 (hereinafter, the amino acid sequence may be referred to as "the motif sequence (i)")

(ii) an amino acid sequence that is derived from an amino acid sequence shown in SEQ ID NO: 1 of which at least one amino acid residue at positions 1 and 2 is substituted by an alanine residue (hereinafter, the amino acid sequence may be referred to as "the motif sequence (ii)").

The motif sequence (i) is an amino acid sequence consisting of VSYKAIR(SEQ ID NO: 1). The arginine residue at position 7 in the amino acid sequence shown in SEQ ID NO: 1 is thought to be involved in selective binding to dendritic cells or vaccine effects. The lysine residue at position 4 in the amino acid sequence shown in SEQ ID NO: 1 is also thought to be involved in selective binding to dendritic cells or vaccine effects.

The motif sequence (ii) is not particularly limited as long as it is an amino acid sequence in which at least one of the 1st and 2nd amino acid residues in the motif sequence (i) is substituted by an alanine residue. However, from the viewpoint of favorably exerting selective binding to dendritic cells or vaccine effects, preferable examples thereof include an amino acid sequence consisting of ASYKAIR (SEQ ID NO: 2) in which the 1st amino acid residue is substituted by an alanine residue and an amino acid sequence consisting of VAYKAIR (SEQ ID NO: 3) in which the 2nd amino acid sequence is substituted by an alanine residue. More preferable examples thereof include an amino acid sequence consisting of SEQ ID NO: 2.

The peptide of the present invention may have only one of the motif sequence (i) or (ii), and may have two or more motif sequences among the motif sequences of (i) and (ii) in which the motif sequences are repeatedly bonded. From the viewpoint of exerting more excellent vaccine effects, the number of the motif sequence(s) contained in the peptide of the present invention is 1 or more, preferably 1 to 10, more preferably 1 to 5, and even more preferably 1 to 3.

In the peptide of the present invention, when two or more motif sequences are repeatedly bonded, the binding between motifs may be such that the C-terminus of one motif sequence and the N-terminus of the other motif sequence are directly linked by a peptide bond. In addition, the C-terminus of one motif sequence and the N-terminus of the other motif sequence may be linked by a peptide bond via a linker sequence consisting of arbitrary amino acid(s) of about 1 to 15, preferably about 1 to 12, and more preferably about 1 to 10. The amino acid sequence of the linker sequence is not particularly limited, but examples thereof include GGGGS (SEQ ID NO: 10) and the like.

From the viewpoint of making the polypeptide of the present invention exert the vaccine effects even more effectively, it is preferable to use a peptide having at least one motif sequence (i), more preferably a peptide having 1 to 5 motif sequences (i) and particularly preferably a peptide having 1 to 3 motif sequences (i).

The peptide of the present invention may be a peptide consisting of at least one motif sequence and, if necessary, a linker sequence provided between each of motif sequences. The amino acid sequence of such a peptide is represented by [Motif Sequence]1-[(Linker Sequence)$_{0\ to\ 1}$ -(Motif Sequence$_1$)]$_{0\ to\ X-1}$ (X is the number of motif sequences contained in the peptide of the present invention).

In addition, the peptide of the present invention may be a peptide in which 1 to 100, preferably 1 to 20, and more preferably 1 to 5 arbitrary amino acid(s) is added to the N-terminal and/or the C-terminal side, in addition to at least one motif sequence and the linker sequence which is provided if necessary. The amino acid sequence of such a peptide is represented by [Added Sequence]$_{0\ to\ 1}$-[Motif Sequence]$_1$-[(Linker Sequence)$_Y$-(Motif Sequence$_1$)]$_{0\ to\ X-1}$-[Added Sequence]$_Z$ (X is the number of motif sequences contained in the peptide of the present invention, Y and Z are 1 or 0, and at least one of Y and Z is 1). However, it is desirable that the C-terminus of the peptide of the present invention is the C-terminus of the motif sequence (that is, it does not have the added sequence at the C-terminus).

[Production Method]

The method for producing the peptide of the present invention is not particularly limited, and may be chemically synthesized by binding amino acids to have a predetermined sequence, or may be produced by using genetic engineering techniques that use a DNA molecule encoding the peptide of the present invention described later.

Hereinafter, a method for producing the peptide of the present invention by a genetic engineering technique is described.

To produce the peptide of the present invention by a genetic engineering technique, a transformant that produces the peptide of the present invention may be cultured.

The transformant producing the peptide of the present invention can be obtained by preparing an expression vector containing a DNA molecule encoding the peptide of the present invention and transforming a host using the expression vector.

The nucleotide sequence of the DNA molecule encoding the peptide of the present invention can be appropriately designed by those skilled in the art according to the amino acid sequence of the peptide of the present invention. For example, examples of the nucleotide sequence encoding the peptide consisting of the amino acid sequence shown in SEQ ID NO: 1 include the nucleotide sequence shown in SEQ ID NO: 4. In addition, for example, examples of the nucleotide sequence encoding the peptide in which three amino acid sequences shown in SEQ ID NO: 1 are linked without via a linker include the nucleotide sequence shown in SEQ ID NO: 5.

The DNA molecule encoding the peptide of the present invention can be obtained by chemical synthesis or can also be obtained by amplification that uses the DNA molecule encoding the peptide of the present invention as a template.

The DNA molecule encoding the peptide of the present invention is preferably one in which the frequency of codon usage is optimized for the host. For example, in the case of using *Escherichia coli* as a host, a DNA molecule optimized for frequency of codon usage in *E. coli* is suitable.

An expression vector containing a DNA molecule encoding the peptide of the present invention includes a regulatory factor such as a promoter operably linked to the DNA molecule. Representative examples of the regulatory factor include a promoter. However, if necessary, a transcriptional element such as an enhancer, a CCAAT box, a TATA box, and an SPI site may be included. In addition, "operably linked to" refers to linkage between various regulatory factors such as promoters, and enhancers that regulate a DNA molecule encoding the peptide of the present invention and the DNA molecule of the present invention in a state of being operable in a host cell. In the expression vector, a transcription termination signal is preferably contained downstream of the DNA molecule. The expression vector may further contain a selection marker gene for selecting a transformant. In addition, as the expression vector, those constructed for gene recombination from phages, plasmids, or viruses that can autonomously propagate in the host are suitable.

The host used for producing the transformant is not particularly limited as long as the expression vector is stable and is capable of autonomously replicating and is capable of expressing a trait of an exogenous gene. Suitable examples thereof include bacteria belonging to the genus *Escherichia* such as *Escherichia coli*, the genus *Bacillus* such as *Bacillus subtilis*, the genus *Pseudomonas* such as *Pseudomonas putida* and the like; yeasts and the like, but other examples include animal cells, insect cells, plant cells and the like. Among them, *E. coli* is particularly preferable.

The transformant can be obtained by introducing the expression vector into a host, and conditions for introducing the expression vector into the host may be appropriately set according to the type of the host and the like. When the host is a bacterium, examples thereof include a method using a competent cell by calcium ion treatment and an electroporation method (electroporation) and the like. When the host is a yeast, examples thereof include an electroporation method, a spheroplast method, a lithium acetate method and the like. When the host is an animal cell, examples thereof include an electroporation method, a calcium phosphate method, a lipofection method and the like.

Culture conditions for the transformant may be appropriately set in consideration of the nutritional physiological properties of the host, but preferable examples include liquid culture. In the case of industrial production, aeration and agitation culture is preferable.

The transformant is cultured, and the culture supernatant or the microbial cells are recovered by a method such as centrifugation of the culture fluid. In the case where the peptide of the present invention is accumulated in the microbial cells, the microbial cells are treated with a mechanical method such as an ultrasonic wave, and a French press or a lytic enzyme such as lysozyme, and if necessary, the microbial cells are solubilized by using an enzyme such as a protease and a surfactant such as sodium dodecyl sulfate (SDS) such that a water-soluble fraction containing the peptide of the present invention can be obtained.

By concentrating the culture fluid or the water-soluble fraction thus obtained, if necessary, and then purifying it using gel filtration, hydrophobic chromatography, ion exchange chromatography, affinity chromatography and the like, the peptide of the present invention can be obtained.

[Use]

When the peptide of the present invention is administered in a state of being fused with an antigenic protein or an antigenic peptide, it binds to dendritic cells and is efficiently incorporated into dendritic cells, whereby excellent vaccine effects are exerted. Accordingly, the peptide of the present invention is used as a carrier peptide for an antigenic protein or an antigenic peptide used for a vaccine to dendritic cells.

In addition, since it is expected that the peptide of the present invention can be conjugated with an adjuvant such as CpG oligodeoxynucleotide to enhance an adjuvant activity by improving the ability of the adjuvant to be delivered to dendritic cells, the peptide of the present invention can also be used as a carrier peptide for an adjuvant to dendritic cells.

2. Fusion Peptide

The fusion peptide of the present invention is a fusion body obtained by binding the peptide to an antigenic protein or an antigenic peptide.

In the fusion peptide of the present invention, the type of the antigen to which the peptide is bound may be any protein or peptide that is capable of inducing an immune response in vivo, and may be appropriately set depending on the type of infectious diseases or diseases to be protected and the like. Examples thereof include an antigenic protein or an antigenic peptide of a pathogenic virus such as influenza virus, avian influenza virus, parainfluenza virus, adenovirus, SARS virus, AIDS virus, cytomegalovirus, hepatitis virus, Zika virus, Japanese encephalitis virus, measles virus, rubella virus, varicella-zoster virus, enterovirus, poliovirus, papillomavirus, herpesvirus, mumps virus, rotavirus, cholera virus, rabies virus, a virus that causes viral hemorrhagic fever (such as Ebola hemorrhagic fever, Marburg disease, Lassa fever, and Crimean-Congo hemorrhagic fever) (preferably, a pathogenic virus such as influenza virus, Zika virus, Japanese encephalitis virus, measles virus, rubella virus, varicella-zoster virus, enterovirus, poliovirus, and mumps virus); an antigenic protein or an antigenic peptide of a pathogenic bacterium such as diphtheria, tetanus, *Mycobacterium tuberculosis, Streptococcus pneumoniae, Neisseria meningitidis, Staphylococcus, Pseudomonas aeruginosa, Bordetella pertussis, Bacillus anthracis, Rickettsia*, and *Salmonella* (preferably, a pathogenic bacterium of diphtheria, tetanus, *Streptococcus pneumoniae, Neisseria meningitidis*, and *Bordetella pertussis*); an antigenic protein or an antigenic peptide of a pathogenic fungus such as *Cryptococcus* and *Aspergillus*; an antigenic protein or an antigenic peptide of a pathogenic organism such as *Plasmodium*; a cancer antigenic protein or a cancer antigenic peptide of malignant melanoma, lung cancer, breast cancer, gastric cancer, esophageal cancer, hepatoma, colon cancer, tongue cancer, thyroid cancer, renal cancer, prostate cancer, uterine cancer, ovarian cancer, pancreatic cancer, biliary tract cancer, skin cancer, pharyngeal cancer, malignant lymphoma, multiple myeloma, leukemia cancer and the like.

In the fusion peptide of the present invention, the peptide (carrier peptide) may be bound to one or both of the N-terminus and the C-terminus of an antigenic protein or an antigenic peptide. From the viewpoint of making vaccine effects to be exerted even more effectively, a preferable embodiment is that the peptide (carrier peptide) is bound to the C-terminus of an antigenic protein or an antigenic peptide.

In the fusion peptide of the present invention, in an embodiment in which the peptide (carrier peptide) is bound to the N-terminus of an antigenic protein or an antigenic peptide, the N-terminus of the antigenic protein or the antigenic peptide and the C-terminus of the peptide (carrier peptide) may be bound directly by a peptide bond or may be bound by a peptide bond via a linker sequence consisting of 1 to 15, preferably 1 to 12, and more preferably 1 to 10 arbitrary amino acids. The amino acid sequence of the linker sequence is not particularly limited, but examples thereof include GGGGS (SEQ ID NO: 10) and the like.

In addition, in the fusion peptide of the present invention, in an embodiment in which the peptide (carrier peptide) is bound to the C-terminus of an antigenic protein or an antigenic peptide, the C-terminus of the antigenic protein or the antigenic peptide and the N-terminus of the peptide (carrier peptide) may be bound directly by a peptide bond or may be bound by a peptide bond via a linker sequence consisting of 1 to 15, preferably 1 to 12, and more preferably 1 to 10 arbitrary amino acids. The amino acid sequence of the linker sequence is not particularly limited, but examples thereof include GGGGS (SEQ ID NO: 10) and the like.

The method for producing the fusion peptide of the present invention is not particularly limited, and, for example, the fusion peptide of the present invention is produced by: a method that includes binding an antigenic protein or an antigenic peptide and the peptide (carrier peptide) via the linker sequence as necessary; a method that includes preparing a DNA molecule encoding the fusion peptide of the present invention and producing the fusion peptide of the present invention by a genetic engineering technique using the DNA molecule; and the like.

The fusion peptide of the present invention can efficiently deliver an antigenic protein or an antigenic peptide to dendritic cells by the peptide (carrier peptide), and can exert excellent vaccine effects without using an adjuvant in some cases, and therefore, the fusion peptide of the present invention can be used as a vaccine.

3. Vaccine Preparation

The vaccine preparation of the present invention includes the fusion peptide. The vaccine preparation of the present invention can be prepared by admixing a pharmaceutically acceptable carrier and an excipient as appropriate in addition to the fusion peptide and formulating according to a known formulation method.

Since the fusion peptide may exert excellent vaccine effects without using an adjuvant in some cases, the vaccine preparation of the present invention need not contain an adjuvant. In the case where the vaccine preparation of the present invention does not contain an adjuvant, an adjuvant may be administered before or after administration of the vaccine, if necessary, to further improve vaccine effects. On the other hand, the vaccine preparation of the present invention may further contain an adjuvant such as CpG oligodeoxynucleotide, Freund, aluminum hydroxide (Alum), and aluminum potassium sulfate to improve vaccine effects further.

The dosage form of the vaccine preparation of the present invention is not particularly limited, but examples thereof include injections, tablets, suppositories, capsules, syrups, microcapsules, patches, aerosols, sprays and the like.

The subject to which the vaccine preparation of the present invention is administered is not particularly limited as long as the subject is an animal in which immunity induction is required by the fusion peptide, and examples thereof include mammals such as human, monkeys, mice, rats, dogs, rabbits, cats, cattle, horses, and goats; Ayes such as chickens and ostriches.

The administration form of the vaccine preparation of the present invention may be either parenteral administration or oral administration and may be appropriately set depending on the type of protective immunity to be induced by an antigenic protein or an antigenic peptide contained in the fusion peptide and the like. Specifically, examples of parenteral administration include intravenous administration, intramuscular administration, intraperitoneal administration, intradermal administration, subcutaneous administration, intraarticular administration, mucosal administration and the like. Examples of the mucosal administration include pulmonary administration, intranasal administration and the like. Among the above-described administration forms, preferable examples include parenteral administration, more preferable examples include intradermal administration, subcutaneous administration, and mucosal administration, further preferable examples include mucosal administration and among mucosal administration, particularly preferable examples include pulmonary administration, from the viewpoint of further improving vaccine effects.

The dose of the vaccine preparation of the present invention may be appropriately set depending on the type of the antigenic protein or antigenic peptide contained in the fusion peptide, the age and body weight of the subject to be administered, expected effects and the like. In the case where the subject animal to be administered is human, the fusion peptide is administered usually in an amount corresponding to 0.01 to 40,000 µg/kg once to several times a day, preferably once a day (initial immunization). In addition, the vaccine preparation of the present invention may be re-administered (booster immunization) under the same conditions as the initial immunization usually after 2 to 6 weeks from the initial immunization.

Examples

Hereinafter, the present invention is described by way of examples. However, the present invention is not construed as being limited to the following examples.

Meanwhile, in the following test examples, unless otherwise indicated, as mouse-derived dendritic cells, dendritic cells (FL-DCs) that were obtained by culturing murine bone marrow cells in the presence of Flt3-L (final concentration 100 ng/ml) for 1 week to induce differentiation were used. In addition, in the following test examples, FL-DCs were analyzed in some cases separately for Plasmacytoid DCs (pDCs), CD11b positive dendritic cells ($CD11b^+$ DCs), and CD11b negative dendritic cells ($CD11b^-$ DCs). Among the mouse-derived dendritic cells, pDCs is a group of CD11c positive and B220 positive cells; $CD11b^+$ DCs is a group of CD11c positive, B220 negative and CD11b positive cells among mouse-derived dendritic cells; $CD11b^-$ DCs is a group of CD11c positive, B220 negative, and CD11b negative cells among mouse-derived dendritic cells.

Test Example 1: Primary Screening of Peptides Selectively Binding to Dendritic Cells Using a phage library displaying about 1 billion kinds of random peptides consisting of 7 or less random amino acids, the following panning operation was performed.

200 µL of a $5 \times 10^{10}$ pfu/mL phage library and $1 \times 10^8$ EL4 cells (murine lymphoma-derived cells) were mixed and were incubated at 25° C. for 60 minutes, followed by centrifugation to recover the supernatant, such that phage clones that did not bind to EL4 cells were recovered. Thereafter, the phage clones were added to $1 \times 10^6$ B16F10 cells (murine melanoma cells) cultured in a 6-well plate, the mixture was incubated at 25° C. for 60 minutes, and then the supernatant was recovered to recover phage clones that did not bind to B16F10 cells. Then, phages were added to $2 \times 10^6$ mouse-derived dendritic cells cultured in a 6-well plate and the mixture was left to stand at 4° C. for 60 minutes. Thereafter, the mixture was washed 10 times with phosphate buffered saline (PBS) and PBS containing 1% NP40 was added to recover the phages. *Escherichia coli* cells were infected with recovered phages and were made to amplify.

When the panning operation was performed twice again using the recovered phages, the number of phages recovered increased (see FIG. 1). From this result, it was suggested that the phage clones that displayed peptides capable of binding to dendritic cells were enriched by performing the panning operation three times in total.

Figure 2:
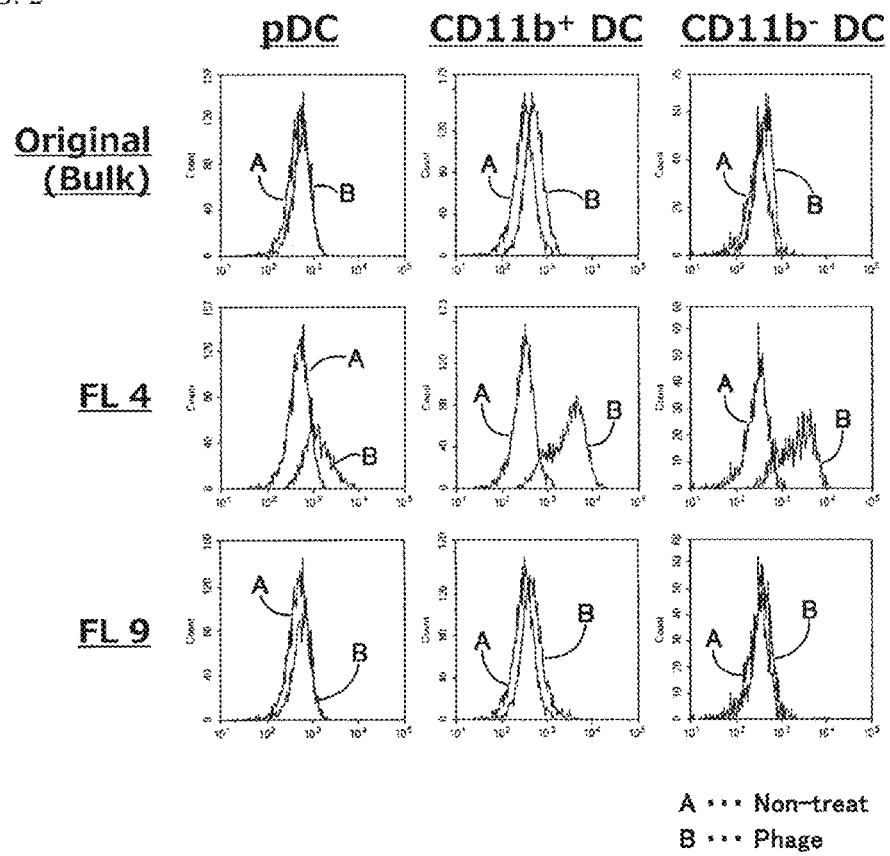
FIG. 2 shows diagrams showing representative examples of results of evaluating the binding of phages to dendritic cells by flow cytometric analysis that is performed by mixing cloned phages and mouse-derived dendritic cells in Test Example 1.

Each of phages recovered by three panning operations was monocloned and amplified. $1 \times 10^5$ mouse-derived dendritic cells and $1.6 \times 10^{10}$ pfu/mL of each phage clone were mixed, and then the phage was assayed for the binding to dendritic cells by flow cytometric analysis using an antibody against the phage. Representative results are shown in FIG. 2. It was confirmed that FL9 did not bind to any dendritic cells, while FL4 (SEQ ID NO: 1) bound to all dendritic cells.

About 60 phage clones obtained were subjected to flow cytometric analysis as described above. As a result, 37 clones shown in Table 1 were identified as clones capable of binding to dendritic cells. Thereafter, in order to identify the amino acid sequence of the surface-displayed peptide of each phage clone capable of binding to dendritic cells, the site where the peptide was inserted in the genome of each phage was amplified by PCR and then sequenced. The obtained results are shown in Table 1. As a result, it was confirmed that many phage clones capable of binding to dendritic cells presented peptides in which the 4th and 7th amino acids from the N-terminus were lysine or arginine.

TABLE 1

| Clone name | Amino acid sequence of displayed peptide | SEQ ID NO |
|---|---|---|
| FL1 | VRKVAVR | 11 |
| FL3 | RDMPVR | 12 |
| FL4 | VSYKAIR | 1 |
| FL5 | ASAKGR | 13 |
| FL7 | ESHRLVR | 14 |
| FL8 | GGSKPVR | 15 |
| FL11 | KLARRS | 16 |
| FL12 | RISAREPR | 17 |
| FL13 | FLEEDAVX | 18 |
| FL16 | AMGKVAR | 19 |
| FL17 | RSQVSVR | 20 |
| FL20 | ASARGPR | 21 |
| FL21 | GRSVR | 22 |
| FL22 | GMPAKRE | 23 |
| FL24 | GNRLGMD | 24 |
| FL25 | GSAKMSR | 25 |
| FL26 | IGSRPIR | 26 |
| FL27 | NRTSQAR | 27 |
| FL28 | PVGRSVR | 28 |

TABLE 1-continued

| Clone name | Amino acid sequence of displayed peptide | SEQ ID NO |
|---|---|---|
| FL29 | VKGRER | 29 |
| FL30 | SARALVR | 30 |
| FL31 | NGVKQAR | 31 |
| FL32 | GLGKGLR | 32 |
| FL33 | DVPKKLR | 33 |
| FL35 | VRLPR | 34 |
| FL38 | GTSHRLR | 35 |
| FL41 | AVRMPLR | 36 |

Test Example 2: Secondary Screening of Peptides Selectively Binding to Dendritic Cells (1) Production of Fusion Peptide A fusion peptide was produced by linking the N-terminus of each peptide which had been made by binding three amino acid sequences of each of FL4, FL5, FL8, and FL20 identified in Test Example 1 directly and tandemly to the C-terminus of PspA. Meanwhile, in the case of FL4, for example, the amino acid sequence of the produced fusion peptide was [Amino acid sequence of PspA]-[VSYKAIR; SEQ ID NO: 1]-[VSYKAIR; SEQ ID NO: 1]-[VSYKAIR; SEQ ID NO: 1].

Specifically, a DNA molecule encoding a peptide which had been made by binding three amino acid sequences of each of FL4, FL5, FL8, and FL20 directly and tandemly was linked to a DNA molecule encoding PspA (SEQ ID NO: 6) via phosphodiester bonds to prepare a DNA molecule encoding a fusion peptide. Then, using the DNA molecule, the transformant was obtained by introducing the DNA molecule into *Escherichia coli* BL21DE3 strain. Subsequently, using the transformant, protein expression was induced with isopropyl-β-thiogalactopyranoside, and the bacteria were harvested and disrupted. Thereafter, the protein was purified with a nickel column and a gel filtration column to obtain a fusion peptide having a predetermined amino acid sequence.

(2) Measurement of PspA-Specific Antibody Titer in Sera in Mice to which Fusion Peptide was Administered 50 μL of physiological saline containing 1 μg of the fusion peptide or PspA in terms of PspA amount was administered into the base of the tail of each of 7-week old C57BL/6J JmsSlc mice (hereinafter sometimes abbreviated as C57BL/6 mice) on Day 0 and Day 10, and blood was collected on Day 17. As a control, a test was also carried out in the case where only physiological saline was administered in the same manner. Further, a test was also carried out in the case where 50 μL of physiological saline containing 10 μg of CpG oligodeoxynucleotide (K3 type, product name "K3 Et-Free", product number "CN-65003" manufactured by GeneDesign Inc.) in addition to 1 μg of the fusion peptide or PspA in terms of PspA amount was administered in the same manner Meanwhile, in these tests, five mice in each group were used.

Figure 3:
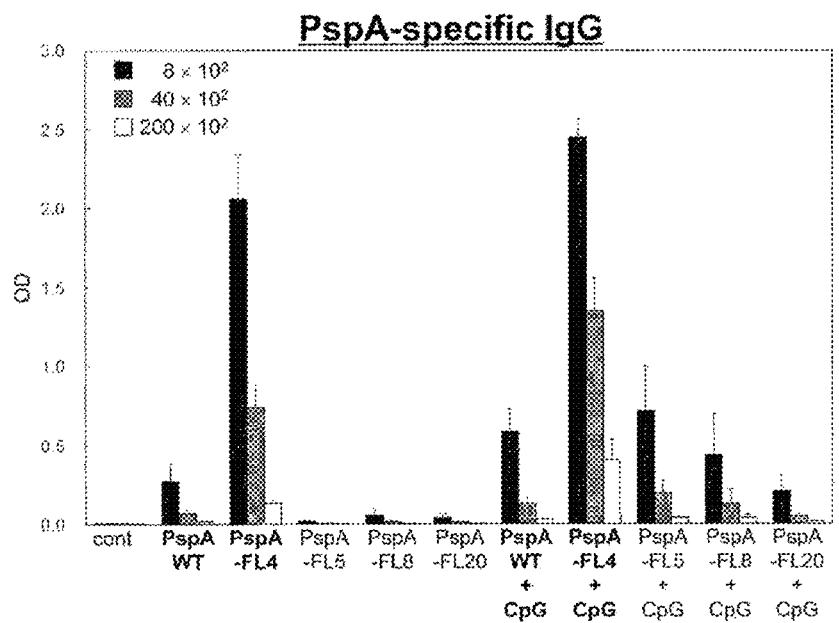
FIG. 3 shows results of measurement of amounts of PspA-specific IgG in sera in mice to which various peptide-fusion bodies were administered in Test Example 2.
Figure 4:
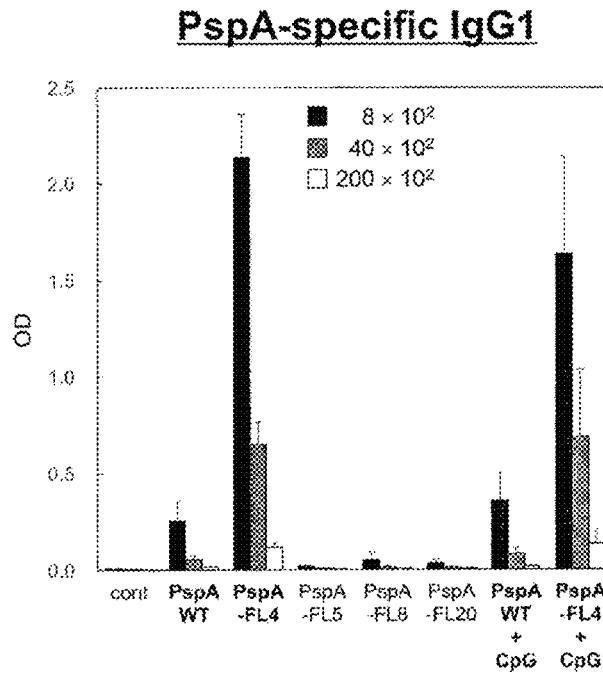
FIG. 4 shows results of measurement of amounts of PspA-specific IgG1 in sera in mice to which various peptide-fusion bodies were administered in Test Example 2.
Figure 5:
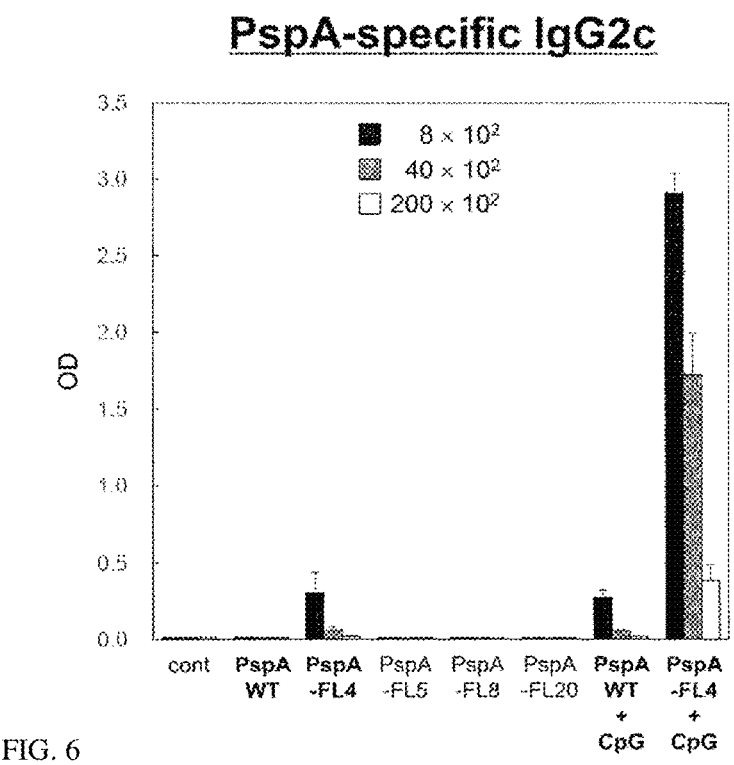
FIG. 5 shows results of measurement of amounts of PspA-specific IgG2c in sera in mice to which various peptide-fusion bodies were administered in Test Example 2.
Figure 6:
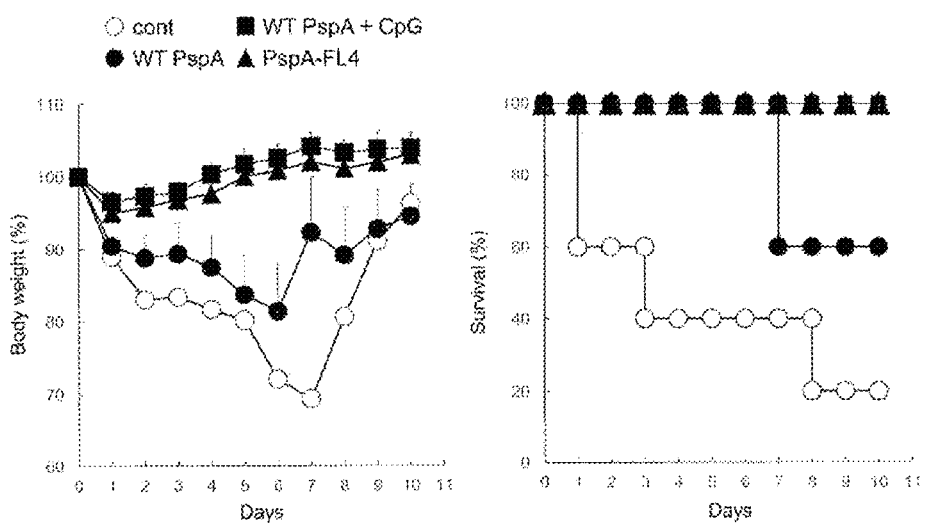
FIG. 6 shows results of observation of body weight change and survival rate over time by administering *Streptococcus pneumoniae* to mice immunized with a fusion peptide in Test Example 3.
Figure 7:
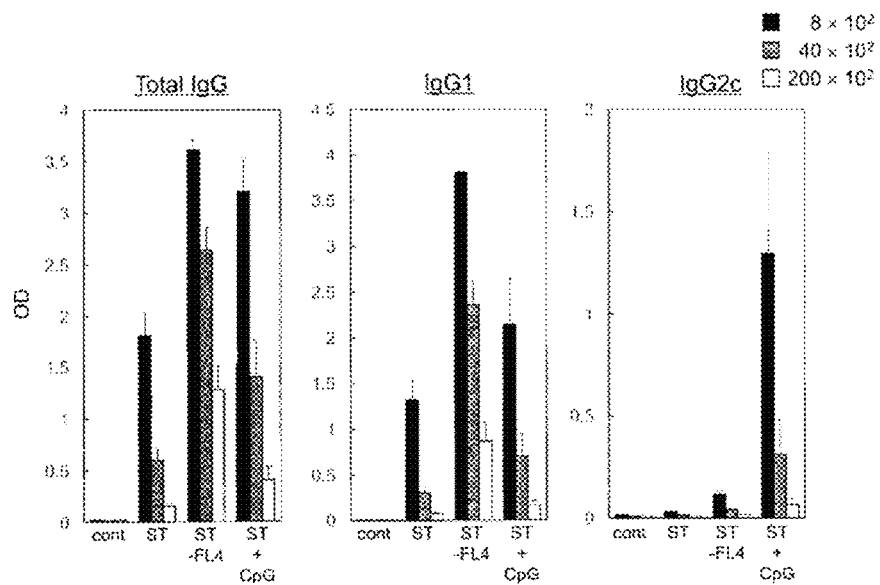
FIG. 7 shows results of measurement of amounts of streptavidin-specific antibodies (total IgG, IgG1, and IgG2c) in sera in mice to which a biotinylated peptide/streptavidin complex was administered in Test Example 4.

Sera were obtained from the blood collected on Day 17 and PspA-specific antibody titers (IgG, IgG1, and IgG2a) in the sera were measured by ELISA. The obtained results are shown in FIGS. 3 to 5. In FIGS. 3 to 5, "PspA WT" refers to PspA, "PspA-FL4" refers to the fusion peptide in which the N-terminus of a peptide obtained by binding three amino acid sequences of FL4 directly and tandemly was linked to the C-terminus of PspA, "PspA WT+CpG" refers to the case where PspA and CpG oligodeoxynucleotide were administered. In addition, in FIGS. 3 to 5, the same meaning applies to the same display format as "PspA-FL4" and "PspA WT+CpG". Further, in FIGS. 3 to 5, "cont" refers to the case where physiological saline was administered. In addition, FIGS. 3 to 5 show each antibody titer (OD value 450 to 570) for each serum dilution ratio ($8\times10^2$, $40\times10^2$, and $200\times10^2$).

As is apparent from FIGS. 3 to 5, among the peptides capable of selectively binding to dendritic cells, it has become clear that the fusion peptide in which the amino acid sequence of FL4 is bound to PspA can remarkably improve the production ability of PspA-specific antibodies. In particular, it was confirmed that the fusion peptide had a remarkably higher PspA-specific antibody titer than when PspA and an adjuvant (CpG oligodeoxynucleotide) were administered at the same time, and when the fusion peptide was used, excellent vaccine effects were exerted without using an adjuvant.

From the above results, it has become clear that a peptide containing the amino acid sequence of FL4 can exert remarkably significant vaccine effects by an antigenic protein or an antigenic peptide, and is useful as a carrier peptide of an antigenic protein or an antigenic peptide.

Test Example 3: Evaluation of Vaccine Effects by Fusion Peptide

The following test was carried out by using a fusion peptide (FL4-PspA, amino acid sequence: [Amino acid sequence of PspA]-[VSYKAIR; SEQ ID NO: 1]-[VSYKAIR; SEQ ID NO: 1]-[VSYKAIR; SEQ ID NO: 1]) that was prepared in Test Example 2, by linking the N-terminus of a peptide obtained by binding three amino acid sequences of FL4 directly and tandemly to the C-terminus of PspA.

Immunity induction was carried out by administering 50 μL of physiological saline containing 1 μg of FL4-PspA or PspA in terms of PspA amount into the base of the tail of each of 7-week old C57BL/6 mice on Day 0 and Day 10. Then, intranasal administration (one of the nostrils of 15 μL) of *Streptococcus pneumoniae* ($1.7\times10^9$ cfu/ml: $5.1\times10^7$ cfu/mouse) was performed on Day 18, and the body weight and survival rate of each mouse after *Streptococcus pneumoniae* administration were determined. In addition, as a control, a test was also carried out in the case where only physiological saline was administered in the same manner without conducting immunization. Further, a test was also carried out in the case where 50 μL of physiological saline containing 10 μg of CpG oligodeoxynucleotide (K3 type, product name "K3 Et-Free", product number "CN-65003" manufactured by GeneDesign Inc.) in addition to 1 μg of FL4-PspA or PspA in terms of PspA amount was administered in the same manner Meanwhile, in these tests, five mice in each group were used.

The obtained results are shown in FIG. 6. Meanwhile, in FIG. 6, the day on which *Streptococcus pneumoniae* was administered is shown as Day 0. In addition, the meanings of the abbreviations in FIG. 6 are as indicated in the column of Test Example 2 above. As a result, in each mouse to which the fusion peptide (FL4-PspA) was administered, no decrease in body weight was observed even after administration of *Streptococcus pneumoniae*, the survival rate was 100% even after 10 days from the administration of *Streptococcus pneumoniae*, and a strong infection protective ability was confirmed.

Test Example 4: Evaluation of Vaccine Effects by Peptide (1) Production of Biotinylated Peptide/Streptavidin Complex A biotinylated peptide in which each of a peptide consisting of the amino acid sequence of FL4, a peptide consisting of the amino acid sequence of FL39 identified in Test Example 1 and a scramble peptide thereof (amino acid sequence: RPSVSRA; SEQ ID NO: 37) was bound to biotin was synthesized. Subsequently, a biotinylated peptide/streptavidin complex was produced by binding streptavidin to each of the obtained biotinylated peptides.

(2) Measurement of Streptavidin-Specific Antibody Titer in Sera in Mice to which the Complex was Administered 50 μL of physiological saline containing 5 μg of the complex or streptavidin in terms of streptavidin amount was administered on Day 0 and Day 10 into the base of the tail of each 7-week old C57BL/6 mouse, and blood was collected on Day 17. As a control, a test was also carried out in the case where only physiological saline was administered in the same manner. Further, a test was also carried out in the case where 50 μL of physiological saline containing 10 μg of CpG oligodeoxynucleotide (K3 type, product name "K3 Et-Free", product number "CN-65003" manufactured by GeneDesign Inc.) in addition to 5 μg of streptavidin was administered in the same manner Meanwhile, in these tests, five mice in each group were used.

Sera were obtained from the blood collected on Day 17 and streptavidin-specific antibody titers (IgG, IgG1, and IgG2a) in the sera were measured by ELISA. The obtained results are shown in FIG. 7. In FIG. 7, "ST" refers to the case where streptavidin was administered, and "ST-FL4" refers to the case where the biotinylated peptide consisting of the amino acid sequence of FL4/streptavidin complex was administered. Further, "cont" refers to the case where physiological saline was administered. In addition, FIG. 7 shows each antibody titer (OD value 450 to 570) for each serum dilution ratio ($8\times10^2$, $40\times10^2$, and $200\times10^2$).

As is apparent from FIG. 7, the production ability of streptavidin-specific antibodies was remarkably excellent in the group where the complex containing the amino acid sequence of FL4 was administered, similarly to the results of Test Example 2.

Test Example 5: Confirmation of Expression of Neuropilin-1 in Dendritic Cells

Since it is known that a peptide having a motif sequence consisting of R/K-X-X-R/K (SEQ ID NO: 1) binds to Neuropilin-1, the expression of Neuropilin-1 on dendritic cells was examined.

Specifically, with regard to FL-DCs of which differentiation was induced by culturing murine bone marrow cells in the presence of Flt3-L (final concentration 100 ng/ml) for 1 week and CD11c positive cells (spleen-derived dendritic cells) purified from the spleen using MACS, the expression of Neuropilin-1 was analyzed separately for pDCs, $CD11b^+$ DCs, and $CD11b^-$ DCs. In addition, murine splenocytes were divided into B cells, $CD4^+$ T cells, and $CD8^+$ T cells, and the expression of Neuropilin-1 was analyzed. Expression of Neuropilin-1 on each cell was confirmed by flow cytometric analysis of each cell with a fluorescently labeled anti-Neuropilin-1 antibody.

Figure 8:
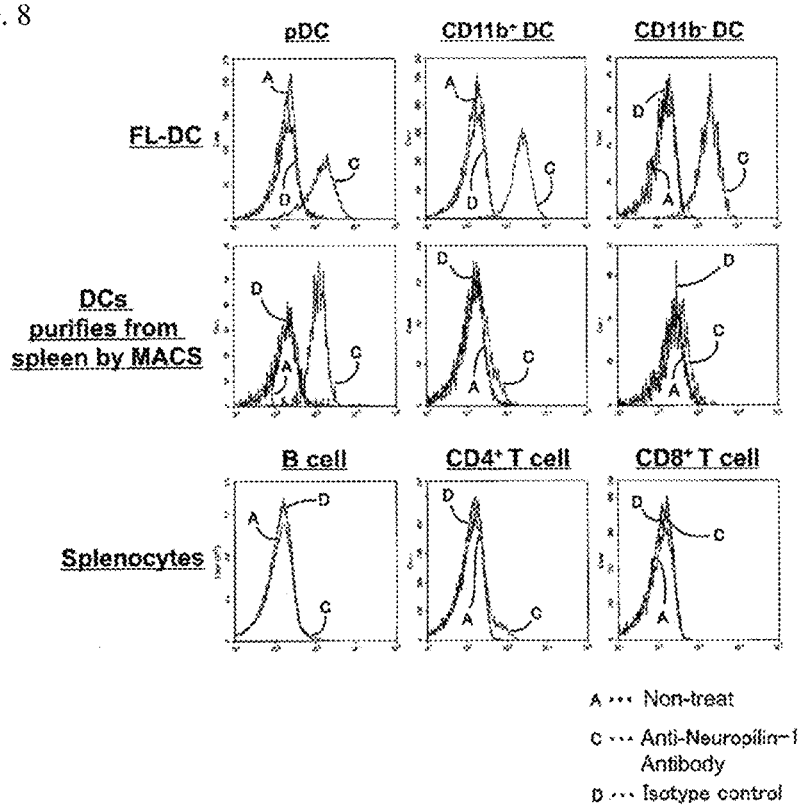
FIG. 8 shows results of evaluating the expression of Neuropilin-1 on dendritic cells and splenocytes by flow cytometric analysis in Test Example 5.

The obtained results are shown in FIG. 8 (horizontal axis: fluorescence intensity, vertical axis: cell number). From the results, strong expression of Neuropilin-1 was observed on all dendritic cells with regard to FL-DCs, but strong expression of Neuropilin-1 was observed only on pDCs with regard to spleen-derived dendritic cells. On the other hand, splenocytes showed some Neuropilin-1 expression on CD4$^+$ T cells. Because there is a report that Neuropilin-1 is expressed on regulatory T cells, the expression of Neuropilin-1 observed on CD4$^+$ T cells of splenocytes is thought to be derived from regulatory T cells.

1. Test Example 6: Evaluation of Binding Ability to Splenocytes Using Phages Displaying Peptides The binding ability to splenocytes was evaluated using phage clones (FL4 and FL8) in which binding to bone marrow-derived dendritic cells was confirmed in Test Example 1. Specifically, 1×10$^5$ splenocytes collected from mice and 1.6×10$^{10}$ pfu/mL of each phage clone were mixed, and the biotinylated antibody to the phage was added. Further, streptavidin modified with a fluorescent dye was added, and the binding of the phage to splenocytes was evaluated by flow cytometric analysis. In addition, as a negative control, a test was conducted in the same manner using a phage clone (FL44) by which binding to bone marrow-derived dendritic cells was not confirmed in Test Example 1.

Figure 9:
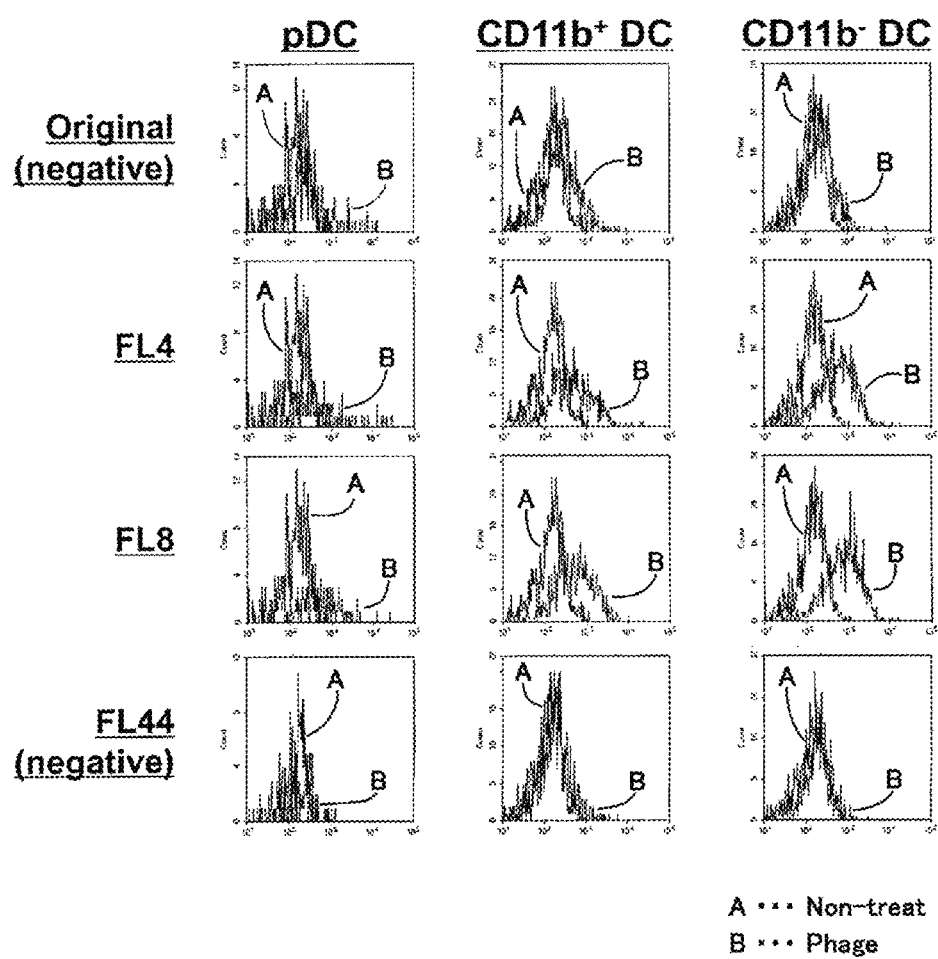
FIG. 9 shows results of evaluating the binding of the phage clones (FL4 and FL8) to dendritic cells contained in splenocytes in Test Example 6.
Figure 10:
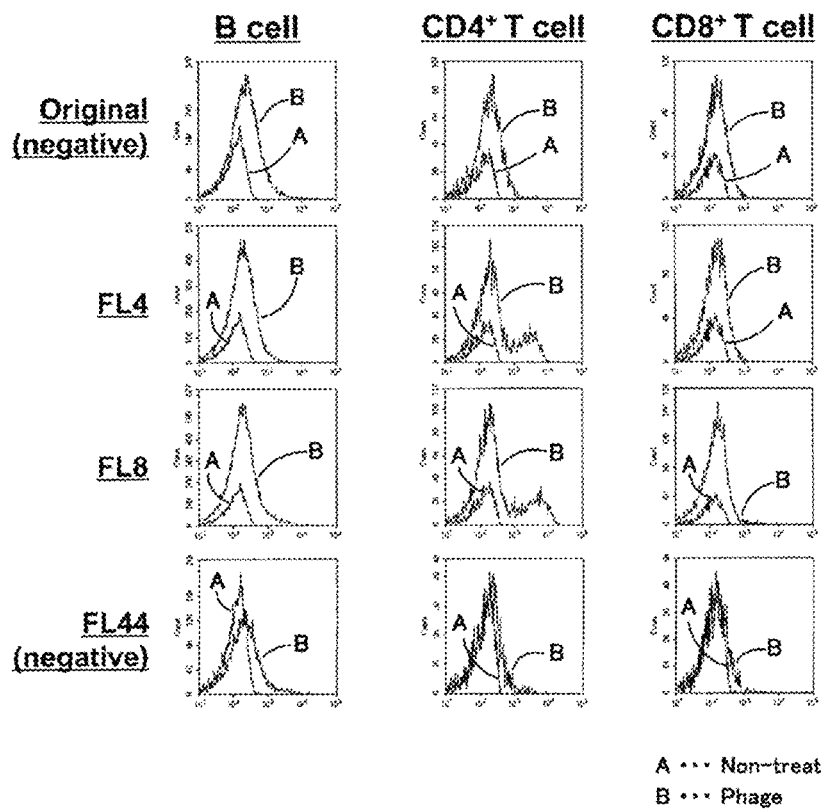
FIG. 10 shows results of evaluating the binding of the phage clones (FL4 and FL8) to B cells, CD4$^+$ T cells and CD8$^+$ T cells contained in splenocytes in Test Example 6.

The obtained results are shown in FIGS. 9 and 10 (horizontal axis: fluorescence intensity, vertical axis: cell number). As is apparent from FIG. 9, phage clones of FL4 and FL8 were confirmed to bind to all dendritic cells contained in splenocytes. In addition, as can be seen from FIG. 10, it was confirmed that these phage clones also bound to CD4$^+$ T cells contained in splenocytes, but it is thought to be due to the expression of Neuropilin-1 on CD4$^+$ T cells (the result of the Test Example 5).

Although the binding ability of the FL4 phage clone to dendritic cells was equivalent to that of FL8, in Test Examples 2 and 4, excellent vaccine effects were observed in the case of using the peptide containing the amino acid sequence of FL4 as compared with the case of using the peptide containing the amino acid sequence of FL8. From these results, it was supported that a peptide containing the amino acid sequence of FL4 has a different effect from other peptides having the motif sequence consisting of R/K-X-X-R/K (SEQ ID NO: 1).

Test Example 7: Evaluation of Binding Ability to Dendritic Cells Using Biotinylated Peptide/Streptavidin Complex (1) Production of Biotinylated Peptide/Streptavidin Complex A biotinylated peptide/streptavidin complex was produced in the same manner as in Test Example 4 above using each of the peptide consisting of the amino acid sequence of FL4 identified in Test Example 1 above and its scramble peptide (amino acid sequence: YRSIVKA; SEQ ID NO: 38). In addition, a biotinylated peptide/streptavidin complex was produced in the same manner as above by using a positive control peptide (amino acid sequence: RPARPAR (SEQ ID NO: 39) which has been reported so far to bind to Neuropilin-1. Meanwhile, streptavidin attached with a fluorescent (PE) label was used.

(2) Measurement of Binding Ability to Dendritic Cells and Splenocytes

Each of various test cells and 0.6 µg of each of various complexes were mixed, and then the binding of each of various complexes to cells was evaluated by flow cytometric analysis. Cells used were 1×10$^5$ FL-DCs, 1×10$^6$ CD11c positive cells purified from the spleen using MACS (the spleen-derived dendritic cells) and 1×10$^6$ murine splenocytes.

Figure 11:
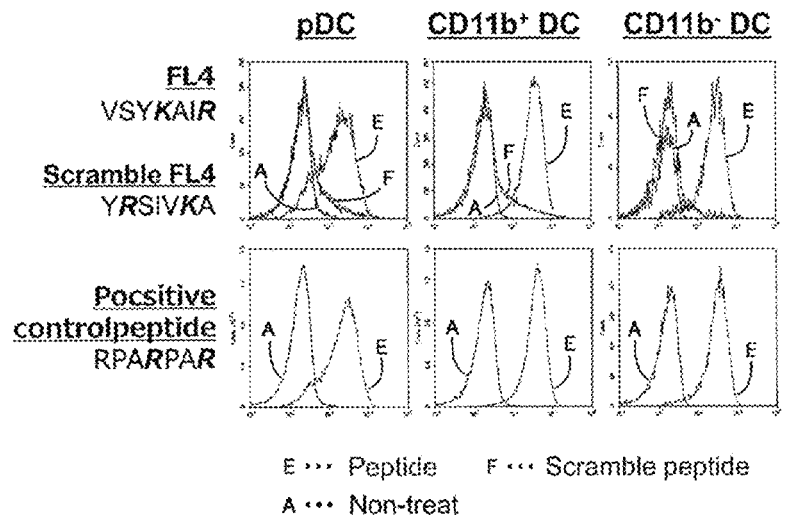
FIG. 11 shows results of evaluating the binding of a biotinylated peptide/streptavidin complex to bone marrow-derived dendritic cells (FL-DCs) in Test Example 7.
Figure 12:
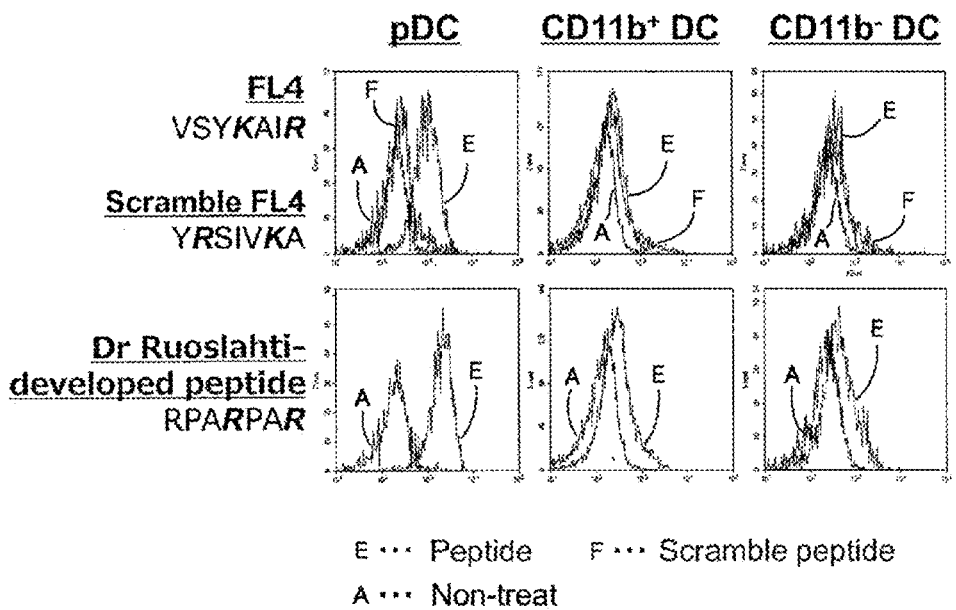
FIG. 12 shows results of evaluating the binding of a biotinylated peptide/streptavidin complex to dendritic cells purified from the spleen in Test Example 7.
Figure 13:
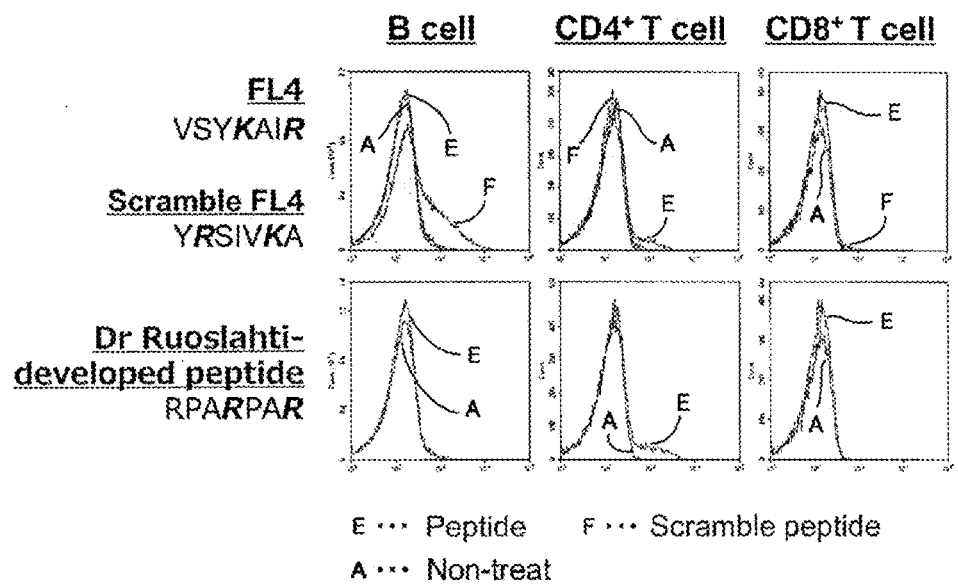
FIG. 13 shows results of evaluating the binding of a biotinylated peptide/streptavidin complex to splenocytes in Test Example 7.

FIG. 11 shows the results of evaluating the binding to FL-DCs, FIG. 12 shows the results of evaluating the binding to dendritic cells purified from the spleen using MACS, and FIG. 13 shows the results of evaluating the binding to murine splenocytes (horizontal axis: fluorescence intensity, vertical axis: cell number). As is apparent from FIGS. 11 and 12, the binding ability was observed for bone marrow-derived dendritic cells regardless of which peptide was used for the biotinylated peptide/streptavidin complex. In addition, as is apparent from FIG. 13, with regard to splenocytes, the weak binding was observed only to CD4 positive cells regardless of which peptide was used for the complex, and the same tendency as in the result of Test Example 6 was confirmed.

That is, also from these test results, it is shown that the binding ability of the peptide consisting of the amino acid sequence of FL4 to dendritic cells was equivalent to that of the peptide consisting of the amino acid sequence of FL8. In Test Examples 2 and 4, excellent vaccine effects were observed by the peptide containing the amino acid sequence of FL4 as compared with those by the peptide containing the amino acid sequence of FL8, and therefore, it is also supported from these test results that the peptide containing the amino acid sequence of FL4 has a different effect from other peptides having the motif sequence consisting of R/K-X-X-R/K (SEQ ID NO: 9).

Test Example 8: Evaluation of CD8$^+$ Cytotoxic T Cells (CTLs) Inducibility (1) Production of Fusion Peptide A fusion peptide (SL8-FL4) was prepared by linking the N-terminus of the peptide consisting of the amino acid sequence of FL4 to the C-terminus of SL8 (SIINFEKL; SEQ ID NO: 40) which is an MHC class I epitope peptide in chicken ovalbumin (OVA). Specifically, the amino acid sequence of the fusion peptide is [Amino acid sequence of SL8 (SIINFEKL; SEQ ID NO: 40)]-[VSYKAIR; SEQ ID NO: 1]. The production method of the fusion peptide was the same as that of PspA-FL4 except that a DNA molecule encoding SL8 was used. In addition, each of peptide-fusion bodies (SL8-F8 and SL8-FL4Scr) in which the peptide was fused with SL8 was prepared using each of FL8 and the scramble peptide of FL4 (FL4Scr, amino acid sequence: YRSIVKA, SEQ ID NO: 41) in the same manner.

(2) Evaluation of Inducibility of CD8$^+$ CTL

50 µL of physiological saline containing 50 µg of each fusion peptide in terms of SL8 amount and 10 µg of CpG oligodeoxynucleotide (K3 type, product name "K3 Et-Free", product number "CN-65003" manufactured by GeneDesign Inc.) was administered subcutaneously into the ears of 7-week old C57BL/6 mice on Day 0, regional lymph nodes were collected on Day 7 and a tetramer assay was performed. In addition, similar tests were conducted with regard to the case where 50 µL, of physiological saline containing 50 μg SL8 alone was administered, the case where 50 μL of physiological saline containing 50 μg SL8 and 50 μg of CpG oligodeoxynucleotide was administered, and the case where only physiological saline was administered (control). Meanwhile, in these tests, five mice in each group were used.

The tetramer assay was carried out as follows. Lymphocytes were recovered from the regional lymph nodes, were stained with fluorescently labeled antibodies against CD44 and CD8 and a fluorescently labeled tetramer recognizing the SL8 peptide presented on H-2K$^b$, then were analyzed using a flow cytometer.

Figure 14:
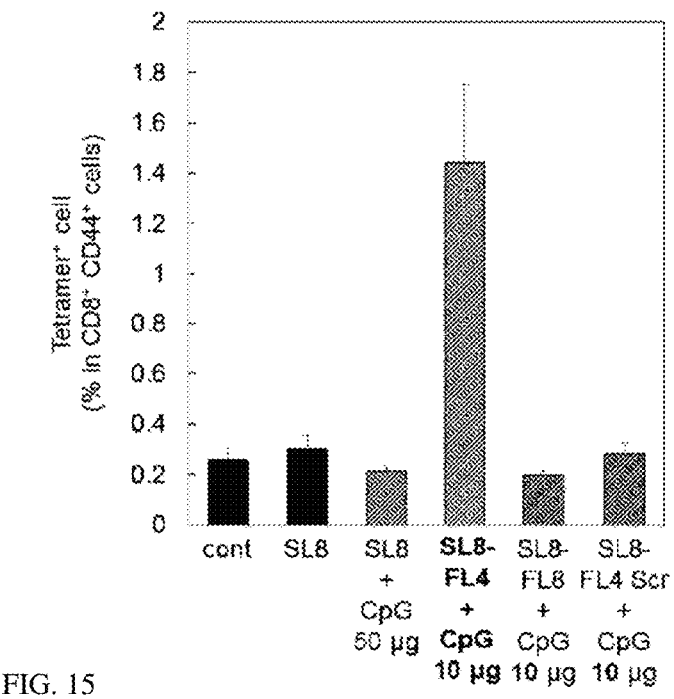
FIG. 14 shows results of a tetramer assay performed on regional lymph nodes of mice to which various peptide-fusion bodies were administered in Test Example 8.

The obtained results are shown in FIG. 14 (horizontal axis: fluorescence intensity, vertical axis: cell number). When SL8 and CpG oligodeoxynucleotide were administered, antigen-specific CD8$^+$ CTLs could not be induced. In addition, each of SL8-FL8 and SL8-FL4Scr could not induce antigen-specific CD8$^+$ CTLs even when being co-administered with CpG oligodeoxynucleotide. On the other hand, when SL8-FL4 and CpG oligodeoxynucleotide were administered, strong induction of antigen-specific CD8$^+$ CTLs was observed.

Test Example 9: Evaluation of CD8$^+$ Cytotoxic T Cells Inducibility

In this test, whether the regression effect of cancer was observed by SL8-specific CD8$^+$ CTLs induced by SL8-FL4 was evaluated. In this test, EG7 cells (cancer cells expressing OVA protein in EL4 cells derived from thymoma of C57BL/6 mouse) were used as cancer cells. Specific test methods are as follows.

1 (10$^6$ EG7 cells were transplanted into the abdomen of 7-week old C57BL/6 mice to prepare tumor bearing mice. 50 μL of physiological saline containing 50 μg of SL8-FL4 in terms of SL8 amount and 50 μg of CpG oligodeoxynucleotide (K3 type, product name "K3 Et-Free", product number "CN-65003" manufactured by GeneDesign Inc.) was administered subcutaneously into the ears of mice after EG7 cells were transplanted and the tumor diameter reached about 5 mm (about 5 days after transplantation). Thereafter, tumor size was measured over time while breeding the mice. In addition, similar tests were carried out with regard to the case where 50 μL of physiological saline containing 50 μg SL8 and 50 μg of CpG oligodeoxynucleotide was administered, and the case where only physiological saline was administered (control). Meanwhile, in these tests, five mice in each group were used.

Figure 15:
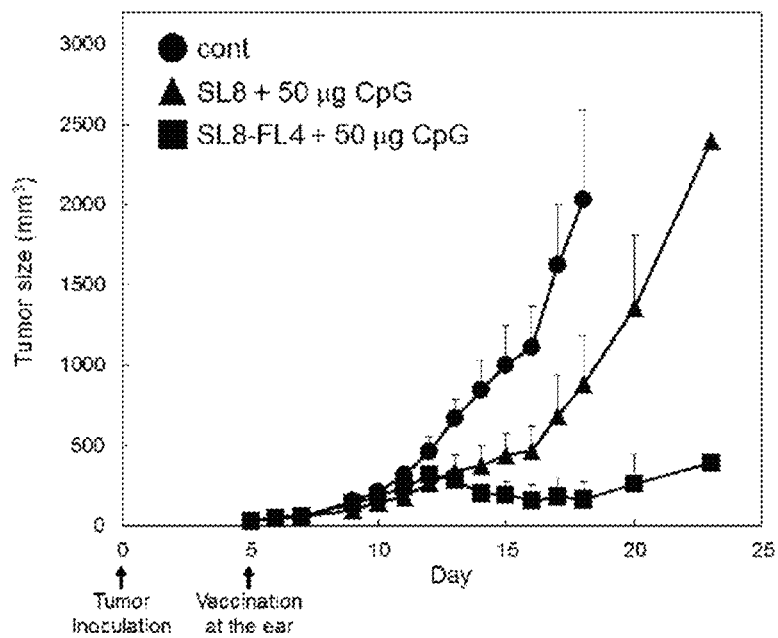
FIG. 15 shows results of measuring the tumor size over time when a fusion peptide of SL8 and FL4 or SL8 was administered to mice transplanted with EG7 cells in Test Example 9.

The obtained results are shown in FIG. 15. When SL8 and CpG oligodeoxynucleotide were co-administered, some tumor regression effects were observed as compared with the case of administration of physiological saline but when SL8-FL4, and CpG oligodeoxynucleotide were co-administered, completely cured mice were observed, and very strong tumor regression effects were observed. That is, from the results, it has become clear that the fusion peptide of FL4 strongly induces antigen-specific CD8$^+$ CTLs even when the tumor is engrafted, and is capable of further inducing the regression effect of tumor.

Test Example 10: Evaluation of CD8$^+$ Cytotoxic T Cells Inducibility Using Peptide Derived from Kras Mutant The Kras gene is a driver gene whose mutation is found in many cancers such as lung cancer, pancreatic cancer, and colon cancer. In particular, the G12D mutation in which the 12th glycine from the N-terminal side of Kras is substituted with aspartic acid is frequently observed. Accordingly, the partial sequence of Kras containing the G12D mutation is expected as a possible target for development of a cancer vaccine as a cancer-specific antigen. Then, in this test, a partial peptide of Kras containing G12D mutation was used to evaluate the antigen-specific CD8$^+$ CTLs inducibility of FL4.

(1) Production of Fusion Peptide

A fusion peptide (G12D-FL4) was prepared by linking the N-terminus of the peptide consisting of the amino acid sequence of FL4 to the C-terminus of a partial peptide of Kras containing G12D mutation (G12D-derived peptide; LVVVGADGV (SEQ ID NO: 42); the 6th to 14th amino acid sequence from the N-terminal side of Kras containing G12D mutation). Specifically, the amino acid sequence of the fusion peptide is [Partial sequence of Kras containing G12D mutation (LVVVGADGV; SEQ ID NO: 42)]-[VSYKAIR; SEQ ID NO: 1]. The production method of the fusion peptide was the same as that of PspA-FL4 except that a DNA molecule encoding the G12D-derived peptide was used.

(2) Measurement of Antigen-Specific CD8$^+$ CTL Response

50 μL of physiological saline containing 50 μg of G12D-FL4 in terms of the G12D-derived peptide amount and 10 μg of CpG oligodeoxynucleotide (K3 type, product name "K3 Et-Free", product number "CN-65003" manufactured by GeneDesign Inc.) was administered subcutaneously into the ears of 7-week old C57BL/6 mice on Day 0, regional lymph nodes were collected on Day 7 and immune cells were recovered. Then, the 1 (10$^6$ recovered immune cells were added to 100 μL of RPMI medium and were cultured at 37° C. for 24 hours, then IFN-γ concentration in the culture fluid was measured. In addition, similar tests were conducted with regard to the case where 50 μL of physiological saline containing 50 μg of the G12D-derived peptide and 10 μg of CpG oligodeoxynucleotide was administered, and the case where only physiological saline was administered (control). Meanwhile, in these tests, five mice in each group were used.

Figure 16:
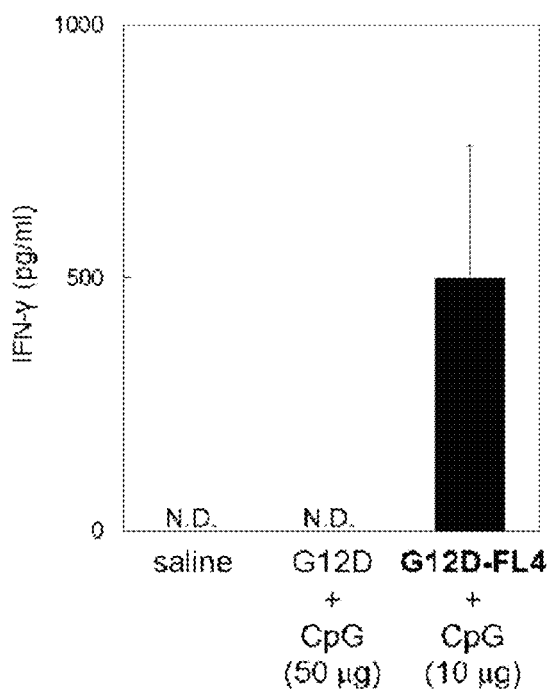
FIG. 16 shows results of evaluating inducibility of antigen-specific CD8+ CTLs (IFN-γ production ability), using immune cells recovered from regional lymph nodes of mice to which a fusion peptide of a G12D-derived peptide and FL4 or a G12D-derived peptide was administered in Test Example 10.

The obtained results are shown in FIG. 16. In the case where the G12D-derived peptide and CpG oligodeoxynucleotide were administered, no induction of antigen-specific CD8$^+$ CTLs could be observed at all. On the other hand, when G12D-FL4 and CpG oligodeoxynucleotide were administered, very strong induction of antigen-specific CD8$^+$ CTLs was observed. It has become clear from these results that FL4 can induce strong vaccine effects not only for a model antigen such as OVA but also for an antigen applicable to cancer vaccines.

Test Example 11: Evaluation of Binding Ability to Dendritic Cells Using Biotinylated Peptide/Streptavidin Complex (1) Production of Biotinylated Peptide A biotinylated peptide was synthesized by linking the N-terminus of each of the peptide consisting of the amino acid sequence of FL4 identified in Test Example 1 and the peptide Mut 1 (amino acid sequence: ASYKAIR (SEQ ID NO: 2)) derived from FL4 of which the 1st amino acid residue was substituted by an alanine residue to biotin.

(2) Measurement of Binding Ability to Dendritic Cells 0.6 μg of each of various biotinylated peptides was added to 1×10$^5$ murine dendritic cells (DC2.4 cells) under the condition of 4° C. and then fluorescent (PE)-labeled streptavidin was added thereto to obtain a biotinylated peptide/ streptavidin complex. Then, the binding of each of various complexes to cells was evaluated by flow cytometric analysis.

Figure 17:
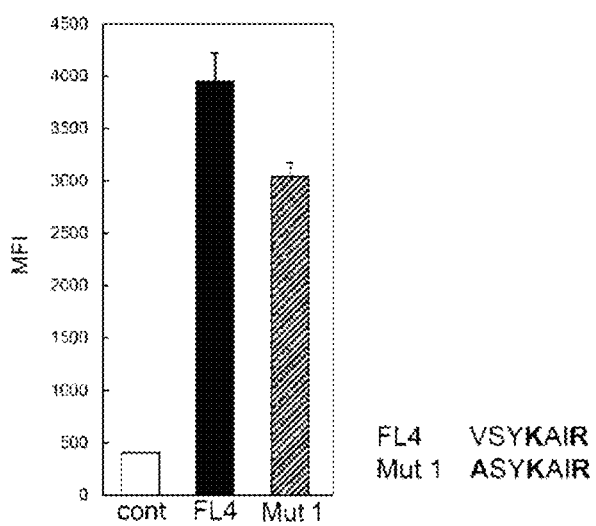
FIG. 17 shows results of evaluating the binding of a biotinylated peptide/streptavidin complex to dendritic cells in Test Example 11.

The results of evaluating the binding to murine dendritic cells are shown in FIG. 17. In FIG. 17, "FL4" and "Mut 1" refer to the biotinylated FL4/streptavidin complex and the biotinylated Mut 1/streptavidin complex, respectively. Further, in FIG. 17, "cont" refers to the case where physiological saline was added instead of a biotinylated peptide. Furthermore, FIG. 17 shows the mean fluorescence intensity "MFI". As is apparent from FIG. 17, the binding ability was observed when any peptide was used.

Test Example 12: Evaluation of Vaccine Effects by Peptide (1) Production of Biotinylated Peptide/NA Complex A biotinylated peptide was synthesized by linking the N-terminus of each of FL4 identified in Test Example 1, a peptide Mut 1 (amino acid sequence: ASYKAIR (SEQ ID NO: 2)) derived from FL4 of which the 1st amino acid residue was substituted by an alanine residue, a peptide Mut 2 (amino acid sequence: VAYKAIR (SEQ ID NO: 3)) derived from FL4 of which the 2nd amino acid residue was substituted by an alanine residue, a peptide Mut 3 (amino acid sequence: VSAKAIR, SEQ ID NO: 43) derived from FL4 of which the 3rd amino acid residue was substituted by an alanine residue, and a peptide Mut 4 (amino acid sequence: VSYKAAR, SEQ ID NO: 44) derived from FL4 of which the 5th amino acid residue was substituted by an alanine residue to biotin. Subsequently, a biotinylated peptide/NeutrAvidin complex was produced by mixing each of the obtained biotinylated peptides and NeutrAvidin.

(2) Measurement of NA-Specific Antibody Titer in Sera in Mice to which the Complex was Administered 50 µL of physiological saline containing 5 µg of the complex or NeutrAvidin in terms of NeutrAvidin amount was administered into the base of the tail of each 7-week old C57BL/6 mouse on Day 0 and Day 10, and blood was collected on Day 17. As a control, a test was also carried out in the case where only physiological saline was administered in the same manner Meanwhile, in these tests, five mice in each group were used.

Figure 18:
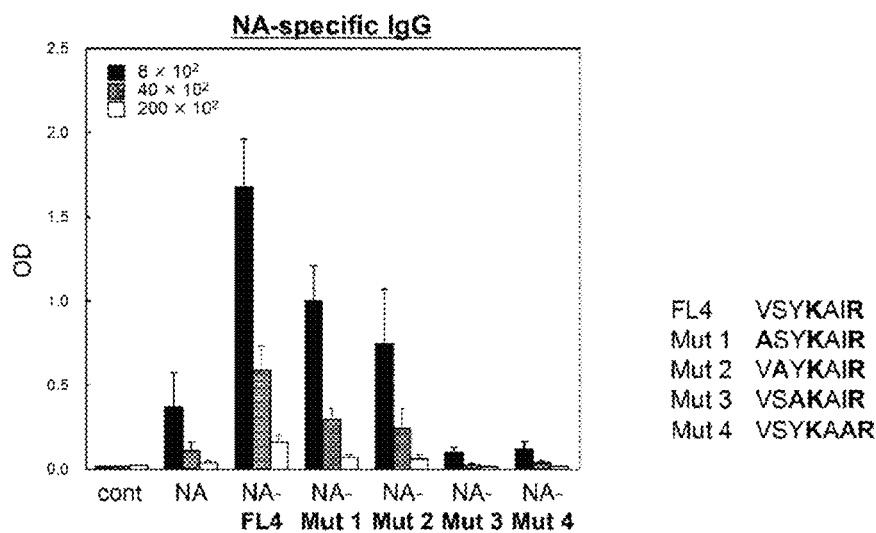
FIG. 18 shows results of measurement of amounts of NeutrAvidin-specific antibodies (total IgG) in sera in mice to which a biotinylated peptide/NeutrAvidin complex was administered in Test Example 12.

Sera were obtained from the blood collected on Day 17 and NeutrAvidin-specific antibody titer (IgG) in the sera was measured by ELISA. The obtained results are shown in FIG. 18. In FIG. 18, "NA" refers to the case of administration of NeutrAvidin, and "NA-FL4" refers to the case of administration of the biotinylated FL4/NeutrAvidin complex. Other peptides are shown in the same display format. Further, in FIG. 18, "cont" refers to the case where physiological saline was administered. In addition, FIG. 18 shows each antibody titer (OD value 450 to 570) for each serum dilution ratio ($8\times10^2$, $40\times10^2$, and $200\times10^2$).

As is apparent from FIG. 18, an excellent production ability of a streptavidin-specific antibody was confirmed in the group where the complex containing each of the amino acid sequence of FL4, the amino acid sequence of Mut 1 and the amino acid sequence of Mut 2 was administered. In the case where each of these amino acid sequences of FL4, Mut 1 and Mut 2 is contained, an excellent antibody-producing ability is recognized unlike the case where each of the amino acid sequences of Mut 3 and Mut 4 is contained, and therefore, it is supported from the test results that a peptide containing the amino acid sequence of each of FL4, Mut 1 and Mut 2 has a different effect from that of a peptide containing the amino acid sequence of each of Mut 3 and Mut 4.

Test Example 13: Evaluation of CD8$^+$ Cytotoxic T Cells Inducibility by Pulmonary Administration It is known that conventional injection vaccines cannot efficiently induce immune responses on the mucosal surface of lung tissues and the like. Accordingly, in the development of therapeutic drugs targeting lung cancer and the like, there is a long-awaited need for a vaccine capable of strongly inducing antigen-specific CD8$^+$ CTLs in lung tissues. Then, in this test, SL8-FL4 was used to evaluate the antigen-specific CD8$^+$ CTLs inducibility via pulmonary administration.

40 µL of physiological saline containing 50 µg of SL8-FL4 in terms of SL8 amount and 10 µg of CpG oligodeoxynucleotide (K3 type, product name "K3 Et-Free", product number "CN-65003" manufactured by GeneDesign Inc.) was pulmonarily administered to 7-week old C57BL/6 mice on Day 0 and Day 7, regional lymph nodes, lung tissues and the spleen were collected on Day 14 and a tetramer assay was performed in the same manner as Test Example 8. In addition, similar tests were conducted with regard to the case where 40 µL of physiological saline containing 50 µg SL8 alone was pulmonarily administered, the case where 50 µL of physiological saline containing 50 µg SL8 and 10 µg of CpG oligodeoxynucleotide was pulmonarily administered, and the case where only physiological saline was pulmonarily administered (control). Meanwhile, in these tests, five mice in each group were used.

Figure 19:
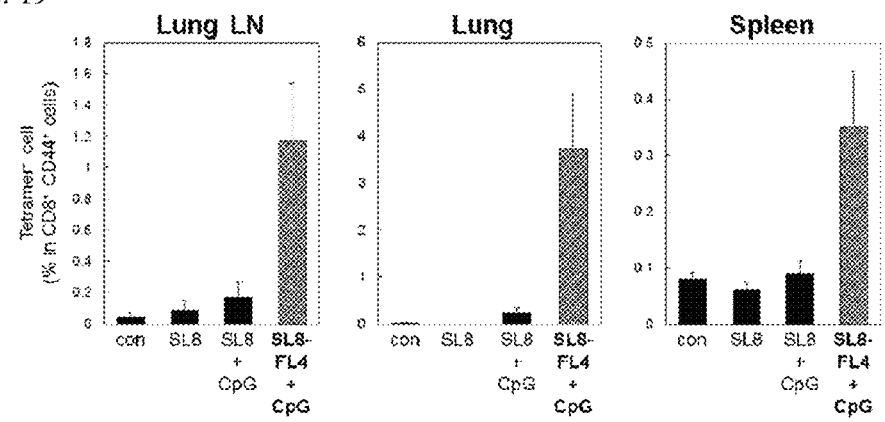
FIG. 19 shows results of a tetramer assay performed on regional lymph nodes in the lungs, lung tissues, and the spleen of mice to which a fusion peptide of SL8 and FL4 was pulmonarily administered in Test Example 13.

The obtained results are shown in FIG. 19. When SL8-FL4 and CpG oligodeoxynucleotide were administered, antigen-specific CD8$^+$ CTLs were strongly induced in regional lymph nodes in the lungs, lung tissues, and the spleen. That is, from the results, it has become clear that the fusion peptide of FL4 can strongly induce antigen-specific CD8$^+$ CTLs even via transmucosal administration.

Test Example 14: Comparative Evaluation of CD8$^+$ Cytotoxic T Cells Inducibility by Pulmonary Administration and Subcutaneous Administration In this study, CD8$^+$ cytotoxic T cells inducibility by pulmonary administration and that by subcutaneous administration were compared by using SL8-FL4. 40 µL of physiological saline containing 50 µg of SL8-FL4 in terms of SL8 amount and 10 µg of CpG oligodeoxynucleotide (K3 type, product name "K3 Et-Free", product number "CN-65003" manufactured by GeneDesign Inc.) was pulmonarily or subcutaneously administered to 7-week old C57BL/6 mice on Day 0 and Day 7, regional lymph nodes and the spleen were collected on Day 14 and a tetramer assay was performed in the same manner as Test Example 8. In addition, a test was also carried out in the case where only physiological saline was subcutaneously administered in the same manner (control). Meanwhile, in these tests, five mice in each group were used.

Figure 20:
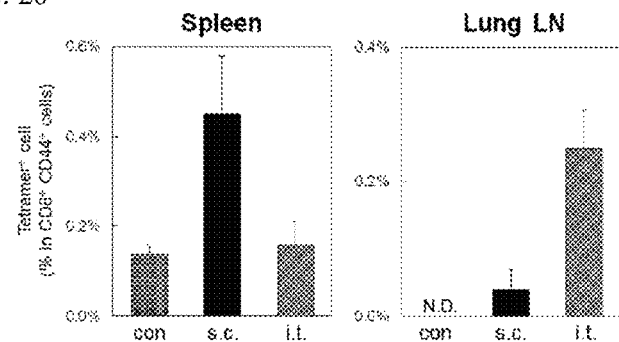
FIG. 20 shows results of a tetramer assay performed on the spleen and regional lymph nodes in the lungs of mice to which a fusion peptide of SL8 and FL4 was pulmonarily administered or subcutaneously administered in Test Example 14.

The obtained results are shown in FIG. 20. Strong induction of antigen-specific CD8$^+$ CTLs in the spleen was observed by subcutaneous administration, whereas strong induction of antigen-specific CD8$^+$ CTLs in regional lymph nodes in the lungs was observed by pulmonary administration. From the above results, it is thought that pulmonary administration of FL4 fusion peptide can strongly induce antigen-specific CD8$^+$ CTLs in lung tissues and regional lymph nodes in the lungs, and can greatly contribute to future development of lung cancer vaccine.

The invention claimed is:

1. A peptide comprising:
   (a) at least one motif sequence selected from the group of amino acid sequences shown in the following (i) and (ii):
      (i) the amino acid sequence shown in SEQ ID NO: 1; and
      (ii) a variant of the amino acid sequence shown in SEQ ID NO: 1 of which at least one amino acid residue at positions 1 and 2 is substituted by an alanine residue, and
   (b) an amino acid sequence of 1 to 100 amino acid(s) located at the N-terminal and/or the C-terminal side of the at least one motif sequence, wherein the amino acid sequence of the 1 to 100 amino acids is not adjacent to the at least one motif sequence in any wild type peptide.

2. The peptide according to claim 1, which has 1 to 5 motif sequences consisting of the amino acid sequence shown in (i).

3. The peptide according to claim 1, wherein the amino acid sequence of 1 to 100 amino acid(s) located at the N-terminal and/or the C-terminal side of the at least one motif sequence comprises an antigenic protein or an antigenic peptide.

4. The peptide according to claim 3, wherein the N-terminus of the at least one motif sequence is bound to the C-terminal side of the antigenic protein or the antigenic peptide.

5. The peptide according to claim 3, wherein the antigenic protein or the antigenic peptide is a cancer antigenic protein or a cancer antigenic peptide.

6. The peptide according to claim 3, wherein the antigenic protein or the antigenic peptide is an antigenic protein or an antigenic peptide of a pathogenic virus.

7. The peptide according to claim 3, wherein the antigenic protein or the antigenic peptide is an antigenic protein or an antigenic peptide of a pathogenic bacterium.

8. An immunogenic preparation comprising the peptide according to claim 3.

9. The immunogenic preparation according to claim 8, which is configured for pulmonary administration.

10. A peptide comprising:
    (a) at least one motif sequence selected from the group of amino acid sequences shown in the following (i) and (ii):
       (i) the amino acid sequence shown in SEQ ID NO: 1; and
       (ii) a variant of the amino acid sequence shown in SEQ ID NO: 1 of which at least one amino acid residue at positions 1 and 2 is substituted by an alanine residue, and
    (b) a First Added Sequence,
    (c) optionally a Second Added Sequence, and
    (d) optionally a Linker Sequence,
    wherein the First Added Sequence comprises an amino acid sequence of 1 to 100 amino acids located at the N-terminal or the C-terminal side of the at least one motif sequence and the optional Second Added Sequence comprises an amino acid sequence of 1 to 100 amino acid(s) located at the other of the N-terminal and/or the C-terminal side of the at least one motif sequence, wherein the First Added Sequence and the Second Added Sequence are not adjacent to the at least one motif sequence in any wild type peptide,
    wherein the peptide is represented by the formula:

(First Added Sequence)$_{0 \text{ to } 1}$-(Motif Sequence)$_1$-[(Linker Sequence)$_Y$-(Motif Sequence)]$_{0 \text{ to } X-1}$-[Second Added Sequence]$_Z$, wherein:
    X is the number of the at least one motif sequence contained in the peptide,
    Y and Z are 1 or 0, and
    at least one of Y and Z is 1.

* * * * *

SEQUENCE LISTING

<160> NUMBER OF SEQ ID NOS: 44

<210> SEQ ID NO 1
<211> LENGTH: 7
<212> TYPE: PRT
<213> ORGANISM: Artificial Sequence
<220> FEATURE:
<223> OTHER INFORMATION: Amino acid sequence of motif sequence

<400> SEQUENCE: 1

Val Ser Tyr Lys Ala Ile Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Amino acid sequence of motif sequence

<400> SEQUENCE: 2

Ala Ser Tyr Lys Ala Ile Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Amino acid sequence of motif sequence

<400> SEQUENCE: 3

Val Ala Tyr Lys Ala Ile Arg
1               5

<210> SEQ ID NO 4
<211> LENGTH: 21
<212> TYPE: DNA
<213> ORGANISM: Artificial Sequence
<220> FEATURE:
<223> OTHER INFORMATION: Base sequence of a peptide having a motif
      sequence

<400> SEQUENCE: 4
gtgagctata aagcgattcg t                                              21

<210> SEQ ID NO 5
<211> LENGTH: 63
<212> TYPE: DNA
<213> ORGANISM: Artificial Sequence
<220> FEATURE:
<223> OTHER INFORMATION: Base sequence of a peptide having three motif
      sequences

<400> SEQUENCE: 5
gtgagctata aagcgattcg tgtgagctat aaagcgattc gtgtgagcta taaagcgatt    60
cgt                                                                 63

<210> SEQ ID NO 6
<211> LENGTH: 1140
<212> TYPE: DNA
<213> ORGANISM: Pneumococcus

<400> SEQUENCE: 6
atggaagaat ctcccgtagc tagtcagtct aaagctgaga aagactatga tgcagcagtg    60

```
aaaaaatctg aagctgctaa gaaggcttac gaagaagcta aaaaagcttt agaggaagca    120
aaagttgcgc aaaaaaaata tgaagacgat caaaagaaaa ctgaagagaa agcagagcta    180
gaaaaagaag cttctgaagc gatagctaag gcaacagaag aagttcaaca agcgtaccta    240
gcttatcaac gagctagcaa caaagccgaa gcagctaaga tgatagaaga ggctcagaga    300
cgcgaaaatg aggcgagagc taaatttact actattcgaa caacaatggt agttcctgaa    360
ccagaacagt tagctgagac taagaaaaaa gcagaagaag ctaaagcaaa agaaccaaaa    420
cttgctaaaa aagcagcaga agctaaagca aaattagaag aggctgagaa aaaagctact    480
gaagccaaac aaaagtgga tgctgaagaa gtcgctcctc aagctaaaat cgctgaattg    540
gaaaatcaag ttcatagact agaacaagag ctcaaagaga ttgatgagtc tgaatcagaa    600
gattatgcta agaaggttt ccgtgctcct cttcaatcta aattggatgc caaaaaagct    660
aaactatcaa aacttgaaga gttaagtgat aagattgatg agttagacgc tgaaattgca    720
aaacttgaag atcaacttaa agctgctgaa gaaacaata atgtagaaga ctactttaaa    780
gaaggtttag agaaaactat tgctgctaaa aaagctgaat tagaaaaaac tgaagctgac    840
cttaagaaag cagttaatga gccagaaaaa tcagctgaag agccatcgca accagagaag    900
ccagctgaag aagctccagc cccagagcaa ccaactgagc caactcaacc agaaaaacca    960
gctgaagaaa ctccagcacc aaaaccagag aagccagctg aacaaccaaa agcagaaaaa   1020
acagatgatc aacaagctga agaagactat gctcgtagat cagaagaaga atataatcgc   1080
ttgactcaac agcaaccgcc aaaagcagaa aaaccagctc ctgcaccaca accagagtaa   1140
```

<210> SEQ ID NO 7
<211> LENGTH: 12
<212> TYPE: PRT
<213> ORGANISM: Artificial Sequence
<220> FEATURE:
<223> OTHER INFORMATION: WH peptide

<400> SEQUENCE: 7

Trp Pro Arg Phe His Ser Ser Val Phe His Thr His
1               5                   10

<210> SEQ ID NO 8
<211> LENGTH: 12
<212> TYPE: PRT
<213> ORGANISM: Artificial Sequence
<220> FEATURE:
<223> OTHER INFORMATION: NW peptide

<400> SEQUENCE: 8

Asn Trp Tyr Leu Pro Trp Leu Gly Thr Asn Asp Trp
1               5                   10

<210> SEQ ID NO 9
<211> LENGTH: 4
<212> TYPE: PRT
<213> ORGANISM: Artificial Sequence
<220> FEATURE:
<223> OTHER INFORMATION: motif sequence
<220> FEATURE:
<221> NAME/KEY: VARIANT
<222> LOCATION: (1)..(1)
<223> OTHER INFORMATION: X is Arg or Lys
<220> FEATURE:
<221> NAME/KEY: VARIANT
<222> LOCATION: (2)..(2)
<223> OTHER INFORMATION: X is any amino acid
<220> FEATURE:
<221> NAME/KEY: VARIANT

```
<222> LOCATION: (3)..(3)
<223> OTHER INFORMATION: X is any amino acid
<220> FEATURE:
<221> NAME/KEY: VARIANT
<222> LOCATION: (4)..(4)
<223> OTHER INFORMATION: X is Arg or Lys

<400> SEQUENCE: 9

Xaa Xaa Xaa Xaa
1

<210> SEQ ID NO 10
<211> LENGTH: 5
<212> TYPE: PRT
<213> ORGANISM: Artificial Sequence
<220> FEATURE:
<223> OTHER INFORMATION: linker peptide

<400> SEQUENCE: 10

Gly Gly Gly Gly Ser
1               5

<210> SEQ ID NO 11
<211> LENGTH: 7
<212> TYPE: PRT
<213> ORGANISM: Artificial Sequence
<220> FEATURE:
<223> OTHER INFORMATION: displayed peptide

<400> SEQUENCE: 11

Val Arg Lys Val Ala Val Arg
1               5

<210> SEQ ID NO 12
<211> LENGTH: 6
<212> TYPE: PRT
<213> ORGANISM: Artificial Sequence
<220> FEATURE:
<223> OTHER INFORMATION: displayed peptide

<400> SEQUENCE: 12

Arg Asp Met Pro Val Arg
1               5

<210> SEQ ID NO 13
<211> LENGTH: 6
<212> TYPE: PRT
<213> ORGANISM: Artificial Sequence
<220> FEATURE:
<223> OTHER INFORMATION: displayed peptide

<400> SEQUENCE: 13

Ala Ser Ala Lys Gly Arg
1               5

<210> SEQ ID NO 14
<211> LENGTH: 7
<212> TYPE: PRT
<213> ORGANISM: Artificial Sequence
<220> FEATURE:
<223> OTHER INFORMATION: displayed peptide

<400> SEQUENCE: 14

Glu Ser His Arg Leu Val Arg
1               5

<210> SEQ ID NO 15
```

```
<211> LENGTH: 7
<212> TYPE: PRT
<213> ORGANISM: Artificial Sequence
<220> FEATURE:
<223> OTHER INFORMATION: displayed peptide

<400> SEQUENCE: 15

Gly Gly Ser Lys Pro Val Arg
1               5

<210> SEQ ID NO 16
<211> LENGTH: 7
<212> TYPE: PRT
<213> ORGANISM: Artificial Sequence
<220> FEATURE:
<223> OTHER INFORMATION: displayed peptide

<400> SEQUENCE: 16

Gly Gly Ser Lys Pro Val Arg
1               5

<210> SEQ ID NO 17
<211> LENGTH: 8
<212> TYPE: PRT
<213> ORGANISM: Artificial Sequence
<220> FEATURE:
<223> OTHER INFORMATION: displayed peptide

<400> SEQUENCE: 17

Arg Ile Ser Ala Arg Glu Pro Arg
1               5

<210> SEQ ID NO 18
<211> LENGTH: 8
<212> TYPE: PRT
<213> ORGANISM: Artificial Sequence
<220> FEATURE:
<223> OTHER INFORMATION: displayed peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 18

Phe Leu Glu Glu Asp Ala Val Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: displayed peptide

<400> SEQUENCE: 19

Ala Met Gly Lys Val Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: displayed peptide

<400> SEQUENCE: 20

Arg Ser Gln Val Ser Val Arg
1               5
```

```
<210> SEQ ID NO 21
<211> LENGTH: 7
<212> TYPE: PRT
<213> ORGANISM: Artificial Sequence
<220> FEATURE:
<223> OTHER INFORMATION: displayed peptide

<400> SEQUENCE: 21

Ala Ser Ala Arg Gly Pro Arg
1               5

<210> SEQ ID NO 22
<211> LENGTH: 5
<212> TYPE: PRT
<213> ORGANISM: Artificial Sequence
<220> FEATURE:
<223> OTHER INFORMATION: displayed peptide

<400> SEQUENCE: 22

Gly Arg Ser Val Arg
1               5

<210> SEQ ID NO 23
<211> LENGTH: 7
<212> TYPE: PRT
<213> ORGANISM: Artificial Sequence
<220> FEATURE:
<223> OTHER INFORMATION: displayed peptide

<400> SEQUENCE: 23

Gly Met Pro Ala Lys Arg Glu
1               5

<210> SEQ ID NO 24
<211> LENGTH: 7
<212> TYPE: PRT
<213> ORGANISM: Artificial Sequence
<220> FEATURE:
<223> OTHER INFORMATION: displayed peptide

<400> SEQUENCE: 24

Gly Asn Arg Leu Gly Met Asp
1               5

<210> SEQ ID NO 25
<211> LENGTH: 7
<212> TYPE: PRT
<213> ORGANISM: Artificial Sequence
<220> FEATURE:
<223> OTHER INFORMATION: displayed peptide

<400> SEQUENCE: 25

Gly Ser Ala Lys Met Ser Arg
1               5

<210> SEQ ID NO 26
<211> LENGTH: 7
<212> TYPE: PRT
<213> ORGANISM: Artificial Sequence
<220> FEATURE:
<223> OTHER INFORMATION: display peptide

<400> SEQUENCE: 26

Ile Gly Ser Arg Pro Ile Arg
1               5
```

```
<210> SEQ ID NO 27
<211> LENGTH: 7
<212> TYPE: PRT
<213> ORGANISM: Artificial Sequence
<220> FEATURE:
<223> OTHER INFORMATION: display peptide

<400> SEQUENCE: 27

Asn Arg Thr Ser Gln Ala Arg
1               5

<210> SEQ ID NO 28
<211> LENGTH: 7
<212> TYPE: PRT
<213> ORGANISM: Artificial Sequence
<220> FEATURE:
<223> OTHER INFORMATION: display peptide

<400> SEQUENCE: 28

Pro Val Gly Arg Ser Val Arg
1               5

<210> SEQ ID NO 29
<211> LENGTH: 6
<212> TYPE: PRT
<213> ORGANISM: Artificial Sequence
<220> FEATURE:
<223> OTHER INFORMATION: display peptide

<400> SEQUENCE: 29

Val Lys Gly Arg Glu Arg
1               5

<210> SEQ ID NO 30
<211> LENGTH: 7
<212> TYPE: PRT
<213> ORGANISM: Artificial Sequence
<220> FEATURE:
<223> OTHER INFORMATION: display peptide

<400> SEQUENCE: 30

Ser Ala Arg Ala Leu Val Arg
1               5

<210> SEQ ID NO 31
<211> LENGTH: 7
<212> TYPE: PRT
<213> ORGANISM: Artificial Sequence
<220> FEATURE:
<223> OTHER INFORMATION: display peptide

<400> SEQUENCE: 31

Asn Gly Val Lys Gln Ala Arg
1               5

<210> SEQ ID NO 32
<211> LENGTH: 7
<212> TYPE: PRT
<213> ORGANISM: Artificial Sequence
<220> FEATURE:
<223> OTHER INFORMATION: display peptide

<400> SEQUENCE: 32

Gly Leu Gly Lys Gly Leu Arg
1               5
```

```
<210> SEQ ID NO 33
<211> LENGTH: 7
<212> TYPE: PRT
<213> ORGANISM: Artificial Sequence
<220> FEATURE:
<223> OTHER INFORMATION: display peptide

<400> SEQUENCE: 33

Asp Val Pro Lys Lys Leu Arg
1               5

<210> SEQ ID NO 34
<211> LENGTH: 5
<212> TYPE: PRT
<213> ORGANISM: Artificial Sequence
<220> FEATURE:
<223> OTHER INFORMATION: display peptide

<400> SEQUENCE: 34

Val Arg Leu Pro Arg
1               5

<210> SEQ ID NO 35
<211> LENGTH: 7
<212> TYPE: PRT
<213> ORGANISM: Artificial Sequence
<220> FEATURE:
<223> OTHER INFORMATION: display peptide

<400> SEQUENCE: 35

Gly Thr Ser His Arg Leu Arg
1               5

<210> SEQ ID NO 36
<211> LENGTH: 7
<212> TYPE: PRT
<213> ORGANISM: Artificial Sequence
<220> FEATURE:
<223> OTHER INFORMATION: display peptide

<400> SEQUENCE: 36

Ala Val Arg Met Pro Leu Arg
1               5

<210> SEQ ID NO 37
<211> LENGTH: 7
<212> TYPE: PRT
<213> ORGANISM: Artificial Sequence
<220> FEATURE:
<223> OTHER INFORMATION: scramble peptide

<400> SEQUENCE: 37

Arg Pro Ser Val Ser Arg Ala
1               5

<210> SEQ ID NO 38
<211> LENGTH: 7
<212> TYPE: PRT
<213> ORGANISM: Artificial Sequence
<220> FEATURE:
<223> OTHER INFORMATION: scramble peptide

<400> SEQUENCE: 38

Tyr Arg Ser Ile Val Lys Ala
1               5

<210> SEQ ID NO 39
```

```
<211> LENGTH: 7
<212> TYPE: PRT
<213> ORGANISM: Artificial Sequence
<220> FEATURE:
<223> OTHER INFORMATION: positive control peptide

<400> SEQUENCE: 39

Arg Pro Ala Arg Pro Ala Arg
1               5

<210> SEQ ID NO 40
<211> LENGTH: 8
<212> TYPE: PRT
<213> ORGANISM: Artificial Sequence
<220> FEATURE:
<223> OTHER INFORMATION: SL8 C-terminus

<400> SEQUENCE: 40

Ser Ile Ile Asn Phe Glu Lys Leu
1               5

<210> SEQ ID NO 41
<211> LENGTH: 7
<212> TYPE: PRT
<213> ORGANISM: Artificial Sequence
<220> FEATURE:
<223> OTHER INFORMATION: scramble of FL4

<400> SEQUENCE: 41

Tyr Arg Ser Ile Val Lys Ala
1               5

<210> SEQ ID NO 42
<211> LENGTH: 9
<212> TYPE: PRT
<213> ORGANISM: Artificial Sequence
<220> FEATURE:
<223> OTHER INFORMATION: G12D-derived peptide

<400> SEQUENCE: 42

Leu Val Val Val Gly Ala Asp Gly Val
1               5

<210> SEQ ID NO 43
<211> LENGTH: 7
<212> TYPE: PRT
<213> ORGANISM: Artificial Sequence
<220> FEATURE:
<223> OTHER INFORMATION: Mut3 peptide

<400> SEQUENCE: 43

Val Ser Ala Lys Ala Ile Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Mut 4 peptide

<400> SEQUENCE: 44

Val Ser Tyr Lys Ala Ala Arg
1               5
```